United States Patent
Cosgrove, III et al.

[11] Patent Number: 6,139,563
[45] Date of Patent: Oct. 31, 2000

[54] SURGICAL DEVICE WITH MALLEABLE SHAFT

[75] Inventors: Delos M. Cosgrove, III, Hunting Valley, Ohio; Joel Donald Gray, Barrington; Donald B. Williams, Lake Forest, both of Ill.; Thomas J. Block, Imperial, Mo.

[73] Assignee: Allegiance Corporation, McGaw Park, Ill.

[21] Appl. No.: 08/936,394

[22] Filed: Sep. 25, 1997

[51] Int. Cl.[7] ....................................... A61B 17/00
[52] U.S. Cl. ............................... 606/205; 600/564
[58] Field of Search ..................... 606/51, 52, 1, 606/17, 205–210, 174; 600/564–568

[56] References Cited

U.S. PATENT DOCUMENTS

| | | |
|---|---|---|
| 1,519,938 | 12/1924 | Smith . |
| 3,162,214 | 12/1964 | Bazinet, Jr. . |
| 3,190,286 | 6/1965 | Stokes . |
| 3,503,398 | 3/1970 | Fogarty et al. . |
| 3,858,578 | 1/1975 | Milo . |
| 4,271,845 | 6/1981 | Chikashige et al. . |
| 4,483,562 | 11/1984 | Schoolman . |
| 4,763,668 | 8/1988 | Macek et al. . |
| 4,817,630 | 4/1989 | Schintgen et al. . |
| 4,936,312 | 6/1990 | Tsukagoshi . |
| 4,945,920 | 8/1990 | Clossick ............................ 600/564 |
| 4,977,887 | 12/1990 | Gouda . |
| 5,002,041 | 3/1991 | Chikama . |
| 5,035,248 | 7/1991 | Zinnecker . |
| 5,058,567 | 10/1991 | Takahashi et al. . |
| 5,100,430 | 3/1992 | Avellanet et al. . |
| 5,133,727 | 7/1992 | Bales et al. . |

(List continued on next page.)

FOREIGN PATENT DOCUMENTS

| | | |
|---|---|---|
| 0 069 942 | 3/1983 | European Pat. Off. . |
| 0 165 472 | 5/1985 | European Pat. Off. . |
| 0 225 045 | 10/1986 | European Pat. Off. . |
| 0 288 309 | 4/1988 | European Pat. Off. . |
| 0 276 104 | 11/1988 | European Pat. Off. . |
| 0 446 020 | 3/1991 | European Pat. Off. . |
| 0 567 146 | 4/1993 | European Pat. Off. . |
| 0 573 817 | 5/1993 | European Pat. Off. . |
| 0 607 594 | 12/1993 | European Pat. Off. . |
| 0 677 275 | 3/1995 | European Pat. Off. . |
| 36 41 935 | 12/1986 | Germany . |
| 3704-094 | 2/1987 | Germany . |
| 38 19 123 | 6/1988 | Germany . |
| 88 08 285 | 6/1988 | Germany . |
| 88 14 560 | 11/1988 | Germany . |
| 89 05 099 | 4/1989 | Germany . |
| 3920-706 | 6/1989 | Germany . |
| 41 36 861 | 11/1991 | Germany . |
| 4243715 A1 | 12/1992 | Germany . |
| 94 04 423 | 3/1994 | Germany . |

(List continued on next page.)

OTHER PUBLICATIONS

Walter Lorenz Surgical, Inc., Cardiovascular Surgery Flexible Vessel Clamps, p. 655.

*Primary Examiner*—Michael Buiz
*Assistant Examiner*—William W. Lewis
*Attorney, Agent, or Firm*—Paul E. Schaafsma; John W. Cornell

[57] ABSTRACT

The present invention provides a surgical device having a tissue engaging portion, a shaft member, and a handle assembly. The tissue engaging portion includes first and second opposed jaws for grasping, securing, and occluding body tissue and conduits. The shaft member is operatively coupled to the tissue engaging portion and is capable of being placed in different curvatures. The handle assembly is operatively coupled to both the shaft member and to the tissue engaging portion. The shaft member of the present invention allows the surgeon to bend and adjust the shape of the surgical device to minimize its intrusion and to allow for proper positioning in predetermined body locations. In a preferred embodiment, a portion of the device is disposable.

165 Claims, 15 Drawing Sheets

U.S. PATENT DOCUMENTS

| | | |
|---|---|---|
| 5,143,475 | 9/1992 | Chikama . |
| 5,152,779 | 10/1992 | Sanagi . |
| 5,156,609 | 10/1992 | Nakao et al. . |
| 5,174,277 | 12/1992 | Matsumaru . |
| 5,178,129 | 1/1993 | Chikama et al. . |
| 5,217,002 | 6/1993 | Katsurada et al. . |
| 5,238,002 | 8/1993 | Devlin et al. . |
| 5,250,073 | 10/1993 | Cottone, Jr. . |
| 5,251,611 | 10/1993 | Zehel et al. . |
| 5,254,130 | 10/1993 | Poncet et al. . |
| 5,271,381 | 12/1993 | Ailinger et al. . |
| 5,318,528 | 6/1994 | Heaven et al. . |
| 5,339,800 | 8/1994 | Wiita et al. . |
| 5,348,259 | 9/1994 | Blanco et al. . |
| 5,372,124 | 12/1994 | Takayama et al. . |
| 5,386,818 | 2/1995 | Schneebaum et al. . |
| 5,419,339 | 5/1995 | Palmer . |
| 5,439,478 | 8/1995 | Palmer . |
| 5,454,378 | 10/1995 | Palmer et al. . |
| 5,454,826 | 10/1995 | Ueda . |
| 5,454,827 | 10/1995 | Aust et al. . |
| 5,467,763 | 11/1995 | McMahon et al. . |
| 5,490,861 | 2/1996 | Kratsch et al. . |
| 5,496,333 | 3/1996 | Sackier et al. . |
| 5,514,115 | 5/1996 | Frantzen . |
| 5,520,222 | 5/1996 | Chikama . |
| 5,522,788 | 6/1996 | Kuzmak . |
| 5,529,820 | 6/1996 | Nomi et al. . |
| 5,535,754 | 7/1996 | Doherty . |
| 5,540,706 | 7/1996 | Aust et al. . |
| 5,542,432 | 8/1996 | Slater et al. . |
| 5,558,665 | 9/1996 | Kieturakis . |
| 5,578,056 | 11/1996 | Pauldrach . |
| 5,593,416 | 1/1997 | Donahue . |
| 5,624,379 | 4/1997 | Ganz et al. . |
| 5,626,607 | 5/1997 | Malecki et al. . |
| 5,643,303 | 7/1997 | Donahue . |

FOREIGN PATENT DOCUMENTS

| | | |
|---|---|---|
| 295 12 503 U | 8/1995 | Germany . |
| WO 91/16856 | 11/1991 | WIPO . |
| WO 93/00048 | 1/1993 | WIPO . |
| WO 93/09835 | 5/1993 | WIPO . |
| WO 93/23760 | 10/1993 | WIPO . |
| WO 94/22377 | 10/1994 | WIPO . |
| WO 95/18574 | 7/1995 | WIPO . |
| WO 95/19144 | 7/1995 | WIPO . |

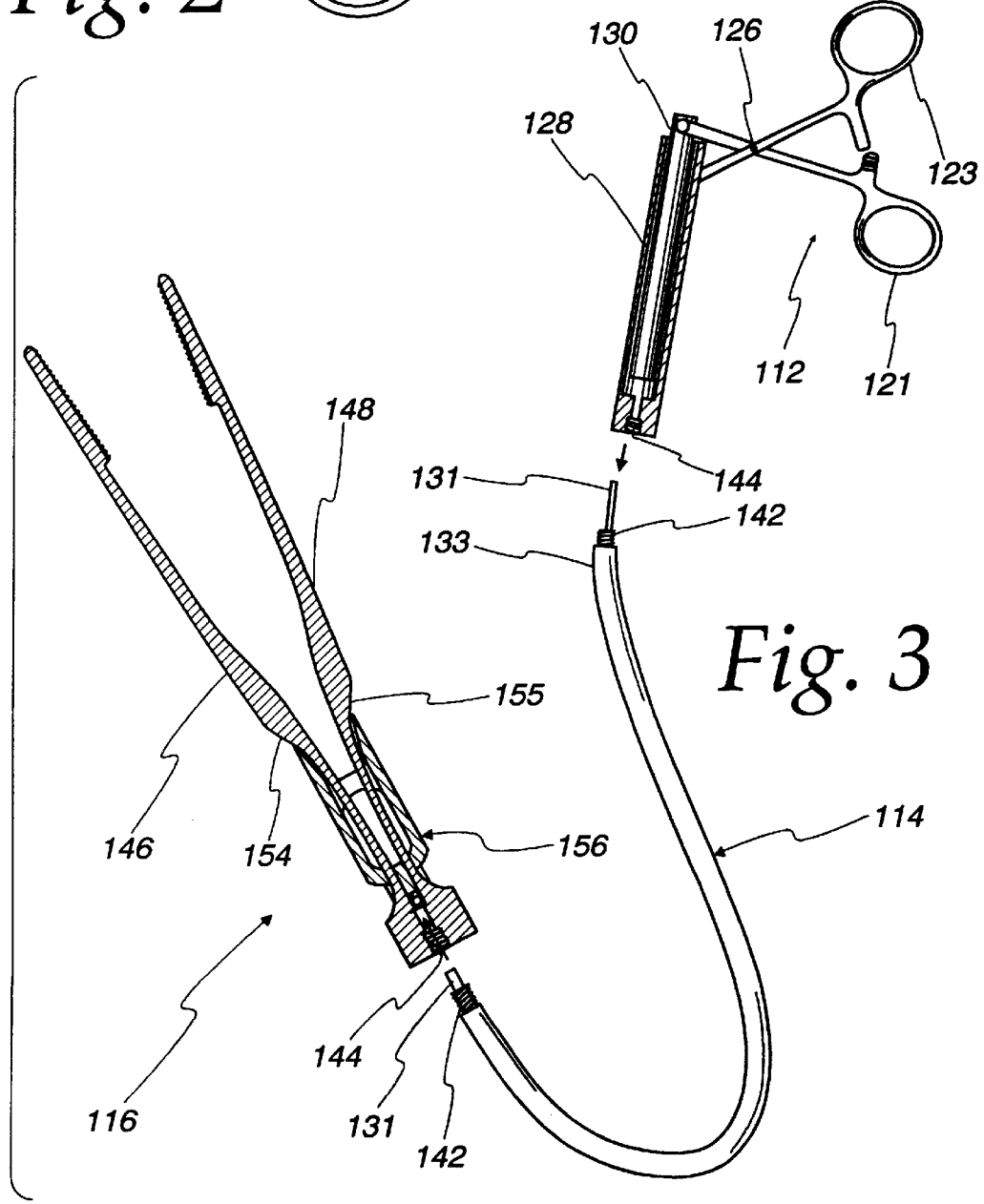

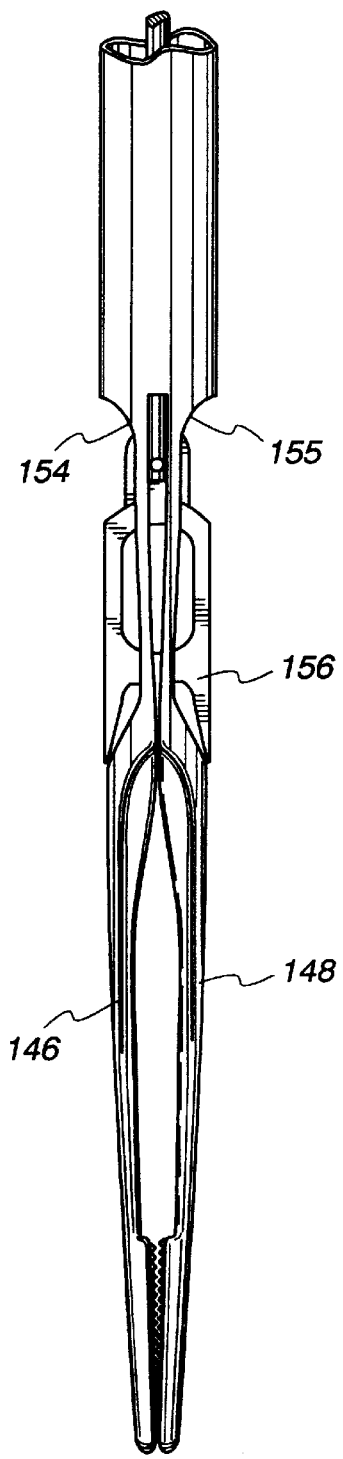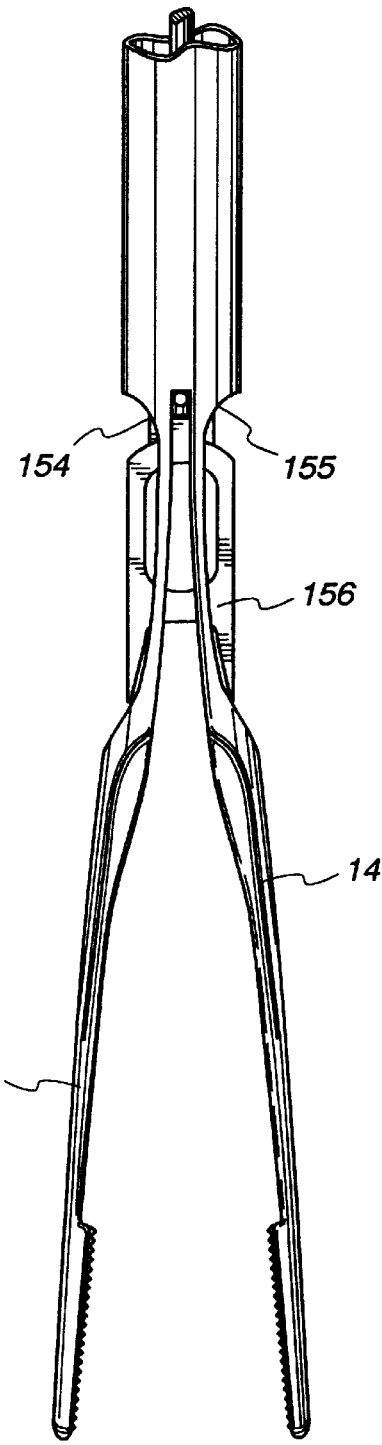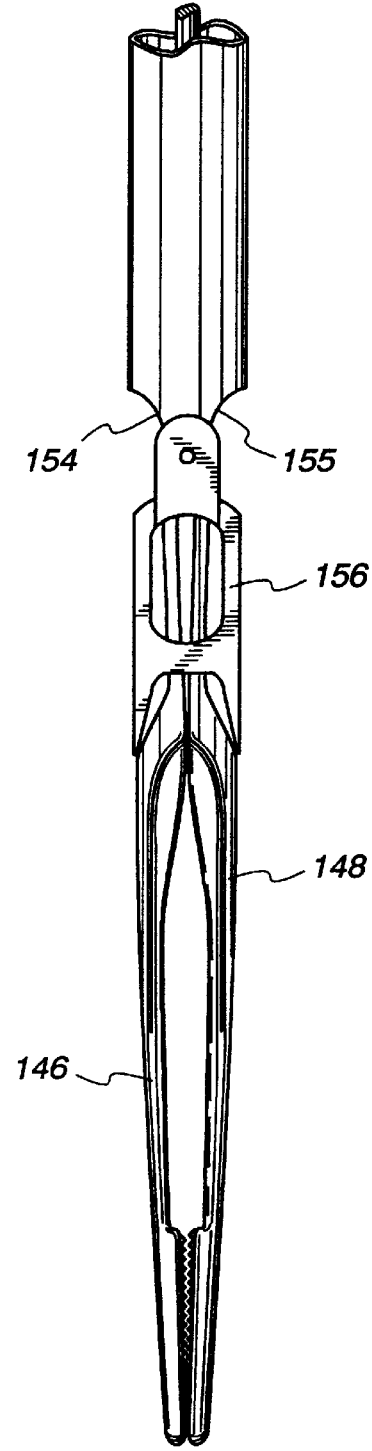

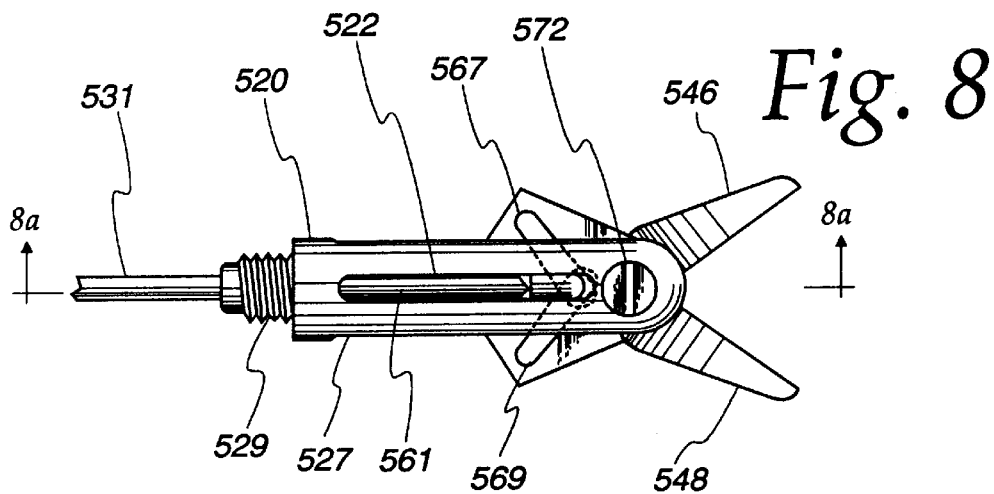
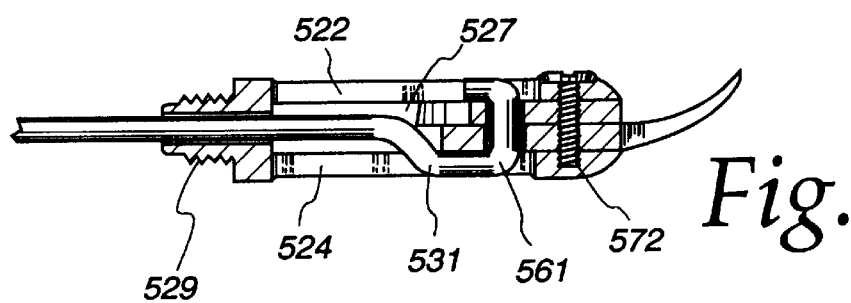
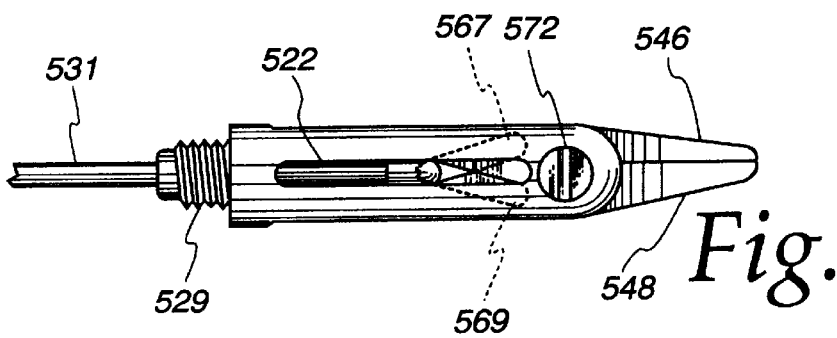
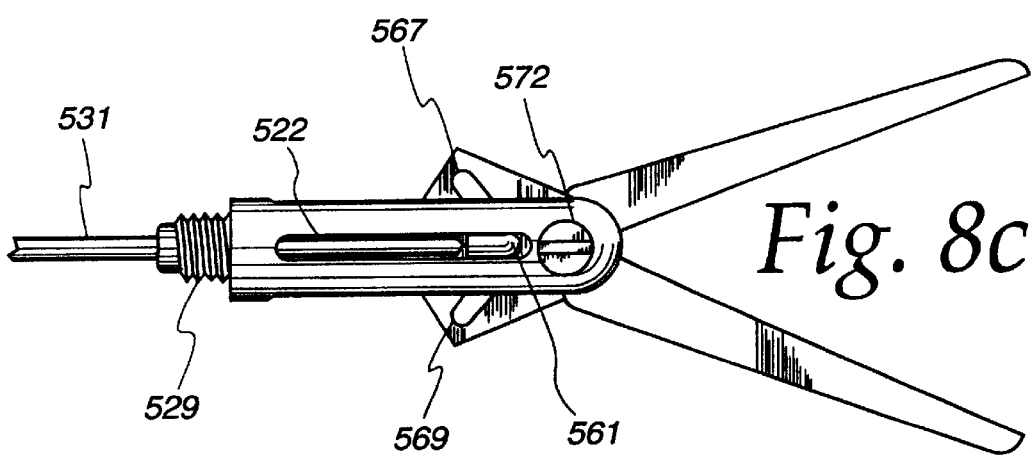

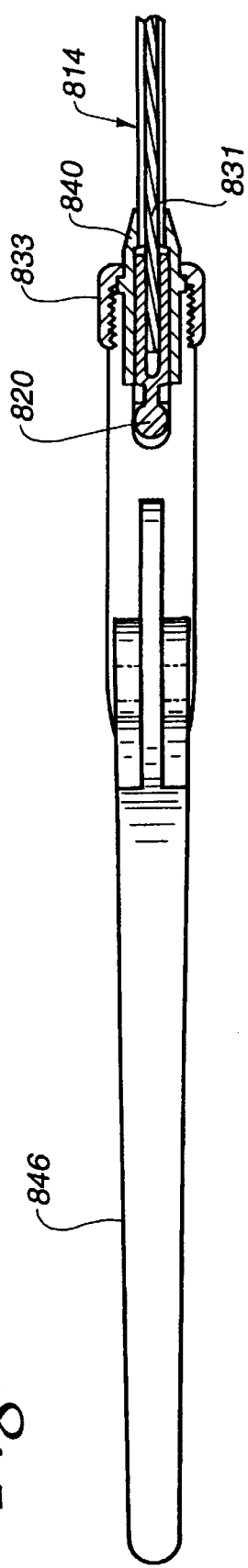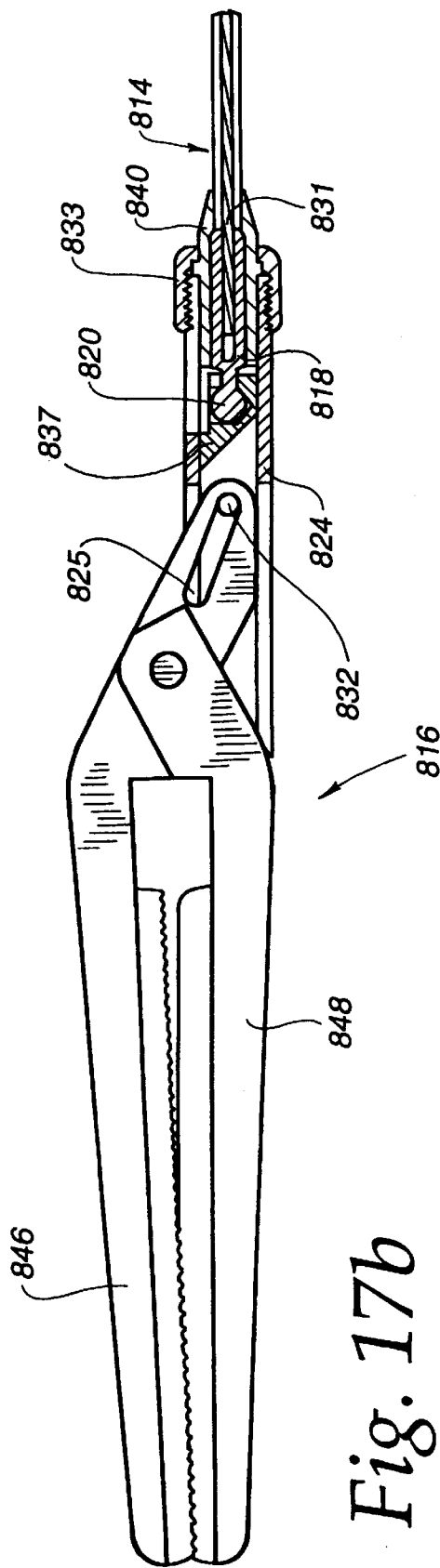

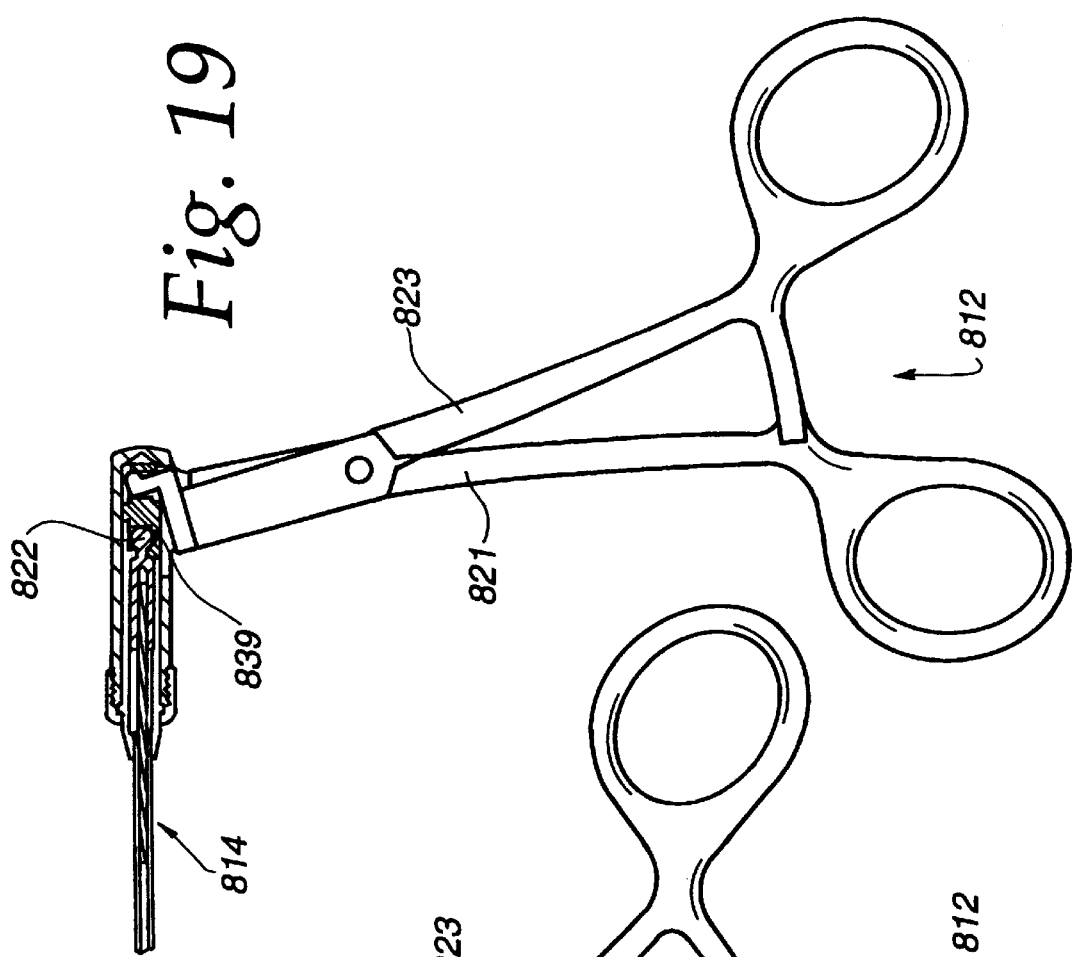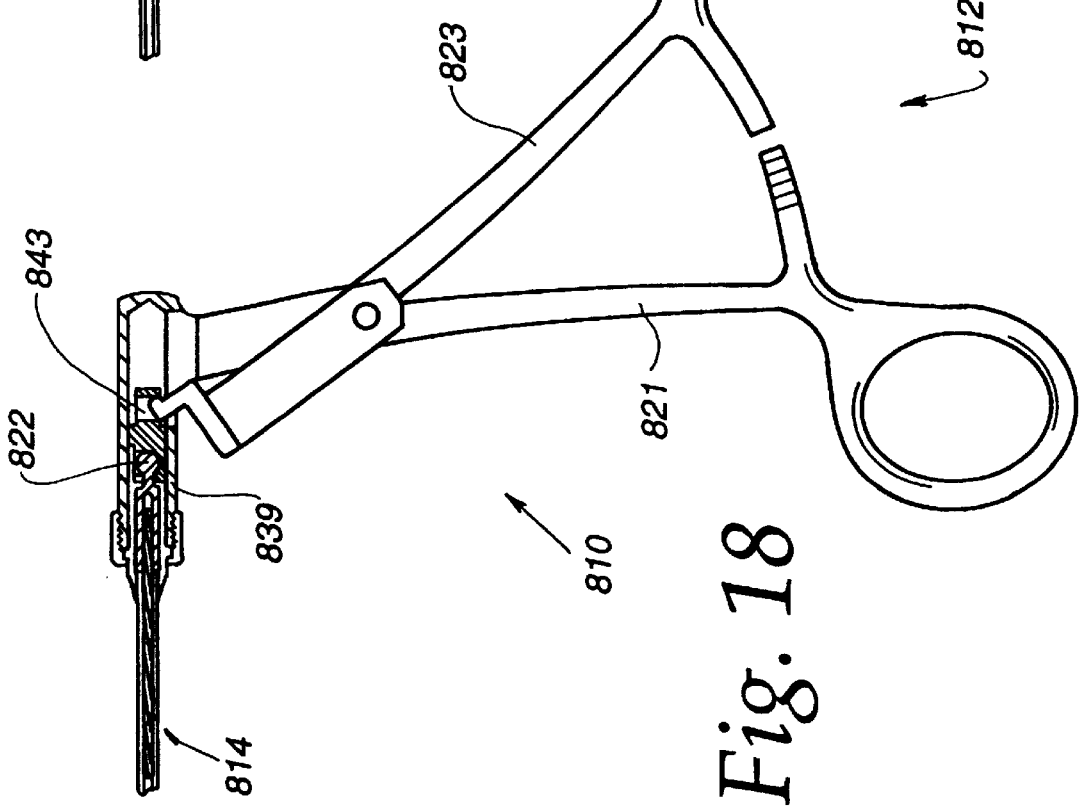

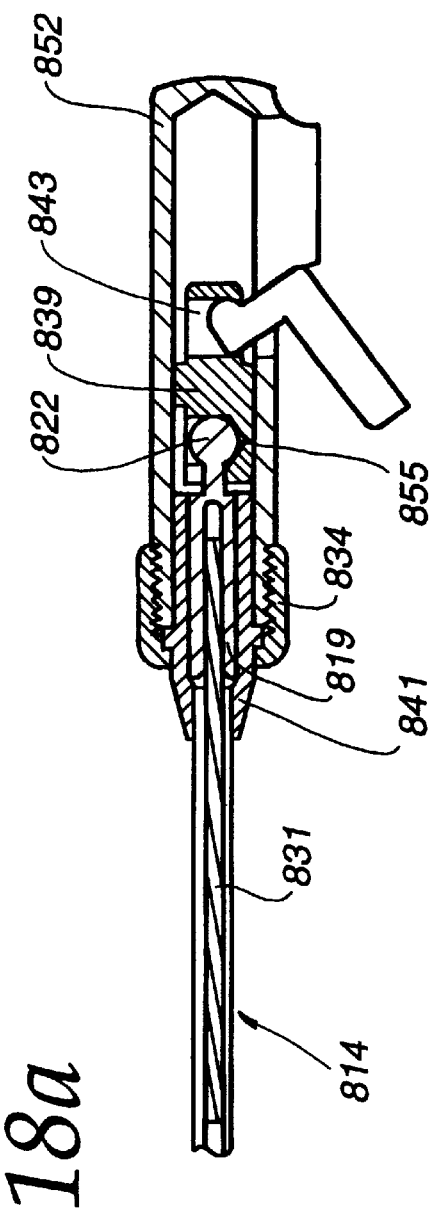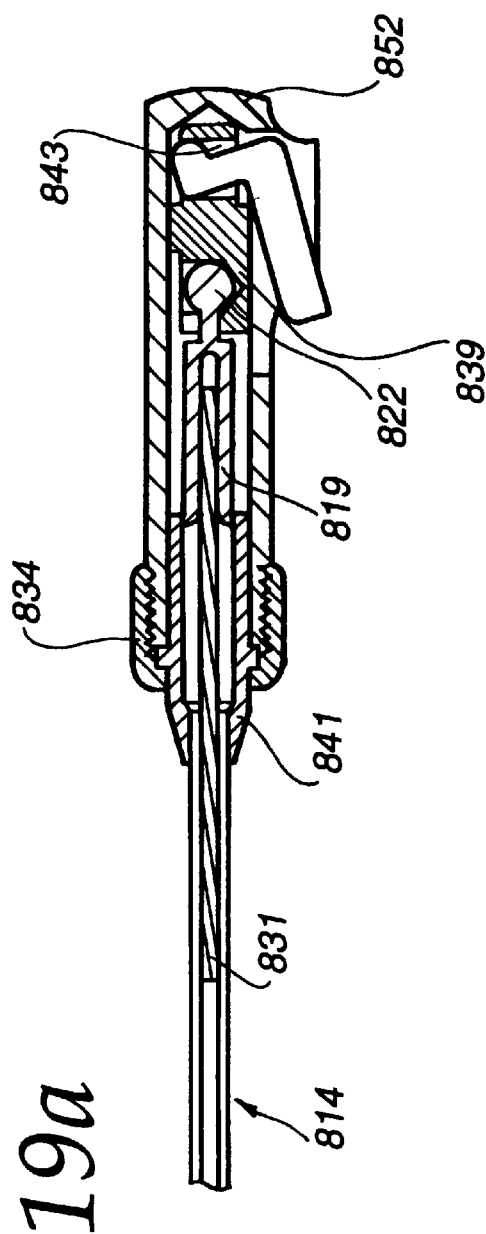

SURGICAL DEVICE WITH MALLEABLE SHAFT

FIELD OF THE INVENTION

This invention relates generally to surgical devices and more specifically to a surgical device with a malleable shaft for use in grasping, securing, and occluding body tissue and conduits.

BACKGROUND OF THE INVENTION

Surgical devices generally include, but are not limited to, clamps, scissors, forceps, dissectors, and retractors. Typically, such surgical devices consist of three elements: a handle, tissue engaging means, and a member extending between the handle and the tissue engaging means. The handle opens and closes the jaws of the tissue engaging means and often has a locking mechanism to hold the jaws closed. The jaws of the tissue engaging means vary extensively in configuration, length, angle, and delicacy depending upon the function of the device and the tissue being engaged. There are many variations of the member provided between the handle and the tissue engaging means. Such members have been provided in a large number of lengths, bends, and angles in order to allow the surgeon to place the jaws in a large number of locations in a wide variety of human body shapes and sizes.

Traditionally, surgeries have been quite invasive to the patient's body, often involving large open incisions. Such surgeries result in great trauma to the patients and require long periods of recovery time. Because these surgeries often involve large incisions, there has not been a strong need for providing surgical devices of a size and detail appropriate for a limited work area. In addition, in order to provide surgeons with a number of choices, surgical devices of various shapes have been provided.

In the recent past, minimally-invasive surgery (MIS) has grown in popularity as an alternative to traditional, large incision surgery. The term MIS refers to performing surgery in smaller incisions in order to reduce the trauma experienced by the patient, increase the speed of healing, and reduce the recovery time. For the patient, this ultimately equates to less time in the hospital which adds to the cost effectiveness of these procedures.

Understandably, it is very challenging for surgeons to perform surgical tasks in small, MIS incisions. The normal concerns of surgery are compounded with the unique problems brought about by MIS procedures. For example, since the objectives of open surgeries and MIS surgeries are often the same, the occluding of body conduits is still of concern. However, surgical devices of the past were designed for occluding of body conduits during open surgery wherein the size of the surgical device was not constrained by narrow diameters of small, MIS incisions. Thus, such surgical devices, which are necessary in most all procedures, protrude out of the MIS incision and have the potential to interfere with the surgeons' hands as they try to visualize, cut, dissect or suture within the incision. Additionally, in the area of non-minimally invasive surgery, the use of instruments has increased as the surgery technique, have become more and more complex.

Thus, it would be advantageous to have a surgical device which minimizes the degree to which it potentially interferes with the surgeon during any surgery, thereby allowing the surgeon to perform more efficient surgery. It would be further advantageous to have a surgical device that allows proper positioning to predetermined body locations within the small incisions.

BRIEF DESCRIPTION OF THE INVENTION

The present invention provides a surgical device which minimizes the degree which it potentially interferes with the surgeon during surgery, particularly but not limited to, MIS. The present invention also provides a surgical device that allows proper positioning to predetermined body locations. The present invention achieves these objectives by utilizing a surgical device with a malleable shaft which allows the surgeon to bend and adjust the shape of the device to minimize its intrusion and to allow for proper positioning in predetermined body locations. The surgical device of the present invention is further provided with tissue engaging means and a handle portion.

BRIEF DESCRIPTION OF THE DRAWINGS

FIG. 2 is a side view of an alternate embodiment of the handle and ratchet assembly of the present invention.

FIG. 2a is a side view of the ratcheting means shown in the assembly of FIG. 2.

FIG. 3 is a side view of an alternate embodiment made in accordance with the principles of the present invention.

FIG. 3a is a side view of the tissue engaging means of the embodiment of FIG. 3, the tissue engaging means being in the closed position.

FIG. 3b is a side view of the tissue engaging means of the embodiment of FIG. 3, the tissue engaging means being in the open position.

FIG. 3c is a cross sectional view of the tissue engaging means of the Embodiment of FIG. 3.

FIG. 8 is a top view of an alternate embodiment of the jaw actuating mechanism made in accordance with the principles of the present invention.

FIG. 8a is a cross-sectional view of the jaw actuating mechanism shown in FIG. 8, taken along the plane of line 8a—8a.

FIG. 8b is a top view of the jaw actuating mechanism shown in FIG. 8, in the closed position.

FIG. 8c is a top view of the jaw actuating mechanism shown in FIG. 8, shown with alternate jaws.

FIG. 15b is a cross-sectional view taken along the plane of line 15a—15a of FIG. 15a.

FIG. 16b is a cross-sectional view taken along the plane of line 16a—16a of FIG. 16a.

FIG. 17a is a top view of the jaw actuating mechanism shown in FIG. 17.

FIG. 17b is a cross-sectional view of the jaw actuating mechanism shown in FIG. 17, in the closed position.

FIGS. 18 and 19 are cross-sectional views of an alternate embodiment of the coupling arrangement between the jaw actuating means and the handle assembly made in accordance with the principles of the present invention.

FIG. 18a is an enlarged view of the coupling arrangement of FIG. 18.

FIG. 19a is an enlarged view of the coupling arrangement of FIG. 19.

DETAILED DESCRIPTION OF THE INVENTION

Figure 1:
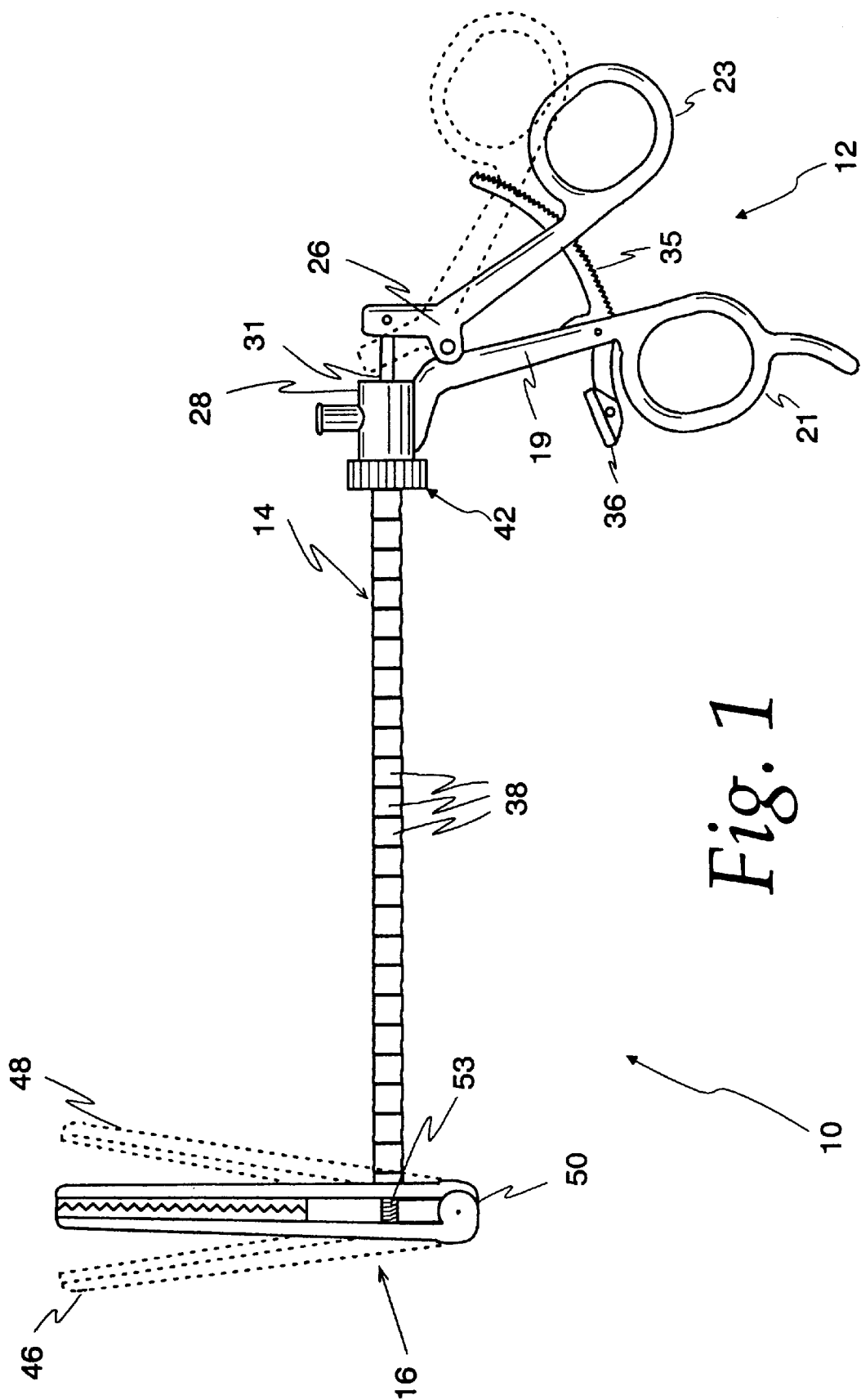
FIG. 1 is a side view of a preferred embodiment made in accordance with the principles of the present invention.

Referring first to FIG. 1, a surgical device 10 made in accordance with the principles of the present invention is shown. The surgical device 10 generally includes a handle portion 12, a shaft member 14, and tissue engaging means 16. Although the figures depict a clamping device, it should be understood that the principles of the present invention are not limited to clamping devices and can be applied to other surgical devices such as, for example, scissors, forceps, dissectors, and retractors.

The handle portion 12 functions to move the tissue engaging means 16 between open and closed positions. The handle portion 12 comprises a ratchet handle assembly 19 having an angled handle. It should be understood that alternate handle assemblies having, different orientations or ratchet designs could also be employed. The handle assembly 19 of the present invention includes a pair of elongate legs 21, 23 which terminate at distal ends with finger grips and which are pivotably connected together at an intermediate location along the lengths thereof at a pivot element 26. A shaft support element 28 for the shaft member 14 is mounted to the proximal end of leg 21. While leg 21 remains stationary with respect to the shaft support element 28, leg 23 moves with respect to leg 21 about the pivot element 26. Additionally, the proximal end of leg 23 is operatively connected to an actuating means 31 which extends axially through the shaft member 14 and is operatively coupled to the tissue engaging means 16. In the preferred embodiment, the actuating means 31 comprises a cable. However, other alternate equivalent actuating means could also be employed.

The handle assembly 19 is further provided with a ratcheting mechanism 35 which is mounted on one of the legs and which interacts with the other leg to hold the tissue engaging means in the closed position. To move the tissue engaging means to the open position, lever 36 is depressed to release leg 23 and the tissue engaging means from the closed position. To move the tissue engaging means from the open position to the closed position, leg 23 is pushed toward leg 21, the proximal end of leg 23 pulling back on the actuating means 31 and thereby actuating the tissue engaging means. Actuation of the tissue engaging means will be discussed in more detail below.

An alternate handle assembly and ratcheting mechanism that could be used with the present invention is shown in FIG. 2. The handle assembly 19 includes two elongate legs 22, 24 operatively coupled together at one end. The legs terminate at distal ends with finger grips. Each of the legs is also provided with a lateral extension 25, 27 carrying ratcheting means 29. The ratcheting means 29 cooperate in the manner shown in FIG. 2a. As the legs are moved relative to one another, the ratcheting means cooperate to set the tissue engaging means of the device in the desired position.

In an alternate embodiment of the handle assembly, shown in FIG. 3, leg 123 can be mounted on a shaft support element 128 for shaft member 114 while leg 121 moves about the pivot element 126. The proximal end of leg 121 is operatively connected to piston 130 which reciprocates axially within shaft support element 128. When leg 121 is moved toward leg 123, leg 121 acts upon piston 130 which in turn pushes on the actuating means 131 The actuating means 131 in turn acts on the tissue engaging means 116.

Figure 4:
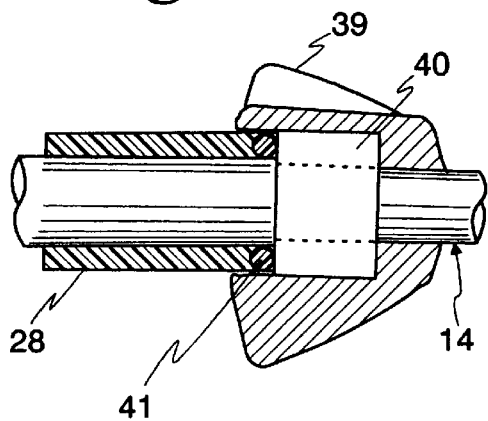
FIG. 4 is a cross-sectional view of the mechanism which enables handle to shaft rotation.

The present invention can also be provided with a mechanism that enables the handle assembly 19 to rotate freely relative to the shaft member 14 to allow the handle to lie flat on the operating table and out of the surgeon's way. FIG. 4 shows the detailed view of this mechanism. As knob 39 is loosened from its attachment with the support element 28 of the handle assembly, the force applied by the knob 39 against bearing 40 and gasket 41 is removed. Consequently, the shaft member 14 can then rotate freely with respect to the support element 28. To set the handle assembly in the desired position with respect to the shaft member, the knob 39 is tightened against the support element 28, thereby acting against the gasket. The gasket 41 thereby functions as a brake, preventing the shaft member to be rotated with respect to the handle assembly after tightening.

The surgical device is further provided with a shaft member 14 which connects the handle assembly 12 to the tissue engaging means 16. As seen in FIG. 1, one end of the shaft member 14 is operatively coupled to the shaft support element 28 of the handle assembly 19 while the opposite end of the shaft member 14 is operatively coupled to the tissue engaging means 16. In the present invention, the shape of the shaft member 14 can be reconfigured in order to enable proper positioning of the tissue engaging means to predetermined body locations. The shaft member 14 can be manipulated to the desired shape to avoid obstructions in an area of work or placed out of the way of the surgeon. It can take a number of forms to accomplish its function.

The shaft member can take a malleable form. Due to its malleable nature, the shaft can be placed in various arrangements to reach desired body locations. In such an embodiment of the present invention, the shaft member comprises a malleable tube with the actuating means extending axially there through. One end of the actuating means is operatively connected to the tissue engaging means while the other end is operatively coupled to the handle assembly. In one embodiment of the present invention, the ends of the actuating means can be coupled to the tissue engaging means and to the handle assembly via a ball and socket coupling. Each end of the actuating means is provided with a member in the shape of a ball which mates with a socket carried by the tissue engaging means and the handle assembly. FIG. 9a is a detailed view of the ball and socket coupling arrangement between the actuating means and the tissue engaging means. However, alternate equivalent coupling means could also be utilized.

Figure 5:
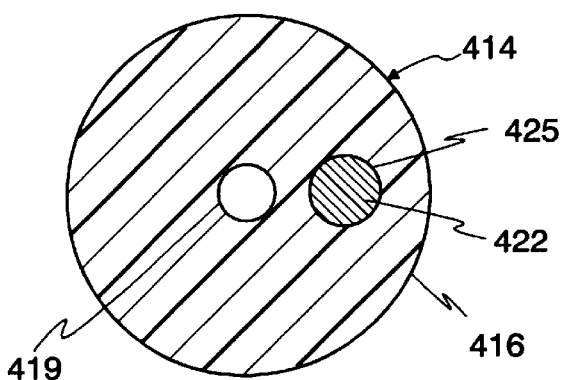
FIG. 5 is a cross-sectional view of a malleable embodiment of the shaft member made in accordance with the principles of the present invention.
Figure 7:
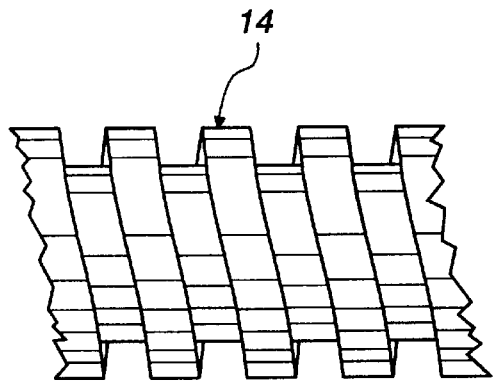
FIG. 7 is a side view of a wound tubing embodiment of the shaft member made in accordance with the principles of the present invention.
Figure 7A:
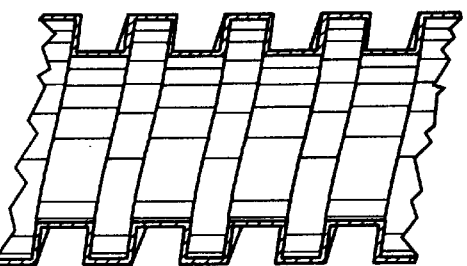
FIG. 7a is a cross-sectional view of the wound tubing embodiment of the shaft member shown in FIG. 7.
Figure 7B:
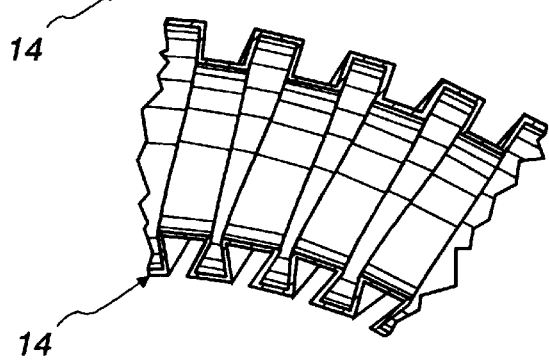
FIG. 7b is a cross-sectional view of the wound tubing embodiment of the shaft member shown in FIG. 7, placed in a bent shape.

The malleable tube of the shaft member could comprise tubing made of soft metal such as, for example, annealed stainless steel, brass, or aluminum, or wound tubing made of steel that is bendable and that can be placed in different shapes. Such a wound tubing embodiment of the shaft member 14 is depicted in FIGS. 7–7b. For a soft metal tube, the bending moment required to create a permanent set in the shaft in the range of approximately 0.5 in-lbs to 8 in-lbs, and preferably approximately 2 in-lbs. Alternately, the shaft member 414 could comprise a dual-channeled tube 416 having the actuating means extending through one channel 419 and a malleable rod 422 extending through the other channel 425 along the length of the tube. The channel 419 housing the jaw actuating means (not shown) preferably extends th rough the center of the tube 416, with the channel 425 housing the malleable rod 422 extending off-center, as shown in FIG. 5. Alternately, the malleable rod 422 can be positioned in other locations in the tube 416 with respect to its center. Due to the presence of the malleable rod 422, the tube 416 can be placed in various shapes. In a further alternate embodiment, a plurality of malleable rods, rather than a single malleable rod, can be employed to keep the tube in the desired shape.

Figure 7C:
FIG. 7c is a side view of a ball and socket embodiment of the shaft member made in accordance with the principles of the present invention.
Figure 7D:
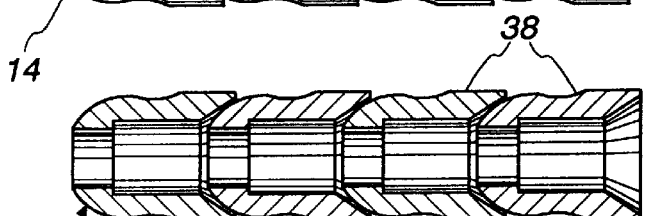
FIG. 7d is a cross-sectional view of the ball and socket embodiment of the shaft member shown in FIG. 7c.
Figure 7E:
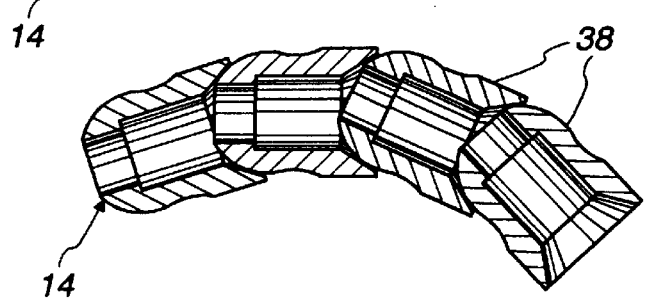
FIG. 7e is a cross-sectional view of the ball and socket embodiment of the shaft member shown in FIG. 7c, placed in a bent shape.

The shaft member can also take a form that is both flexible and rigid. This form has the ability to be flexible so that the surgeon can form a predetermined shape to fit into a particular body opening and pathway. The state of the shaft can be changed from rigid to flexible and vice versa. Such an embodiment of the present invention is shown in FIG. 1 and in detail in FIGS. 7c–7e. The shaft member 14 comprises a series of interconnected ball and socket segments 38 through which the actuating cable 31 passes. FIGS. 7d–7e show the cross-section of a typical ball and socket segment, while FIG. 7e shows the interaction between adjacent segments when the shaft member is placed in a desired shape. Referring back to FIG. 1, a tightening knob 42 is also provided adjacent the shaft support element 28 which can be actuated in order to exert axial compression on the segments 38. This compression allows the ball and socket segments 38 of the shaft member 14 to be locked in any shape selected by the surgeon or other user of the surgical device.

Alternately, the shaft member comprises a flexible tube with the actuating cable extending axially there through. A second applier instrument that is malleable grasps the shaft member and together the two are inserted into the incision. Once the tissue engaging means are in the closed position, the applier instrument is released and removed.

The surgical device is further provided with a tissue engaging means 16 which functions to grasp, secure, and occlude body tissue and conduits. The tissue engaging means 16 includes a pair of jaws 46, 48, the jaws being connected at one end by a hinge 50. The jaws are moveable by various mechanisms between an open position and a closed position. The tissue engaging means can also be provided with a compression return spring 53 to assist the jaws in returning to the open position.

Since it is important to surgeons to reduce the size and bulk of the hinge of the jaws in order to increase visualization and to minimize the space the tissue engaging means occupies, in one embodiment of the present invention, the jaws are coaxial with the longitudinal axis of the shaft member. This orientation, which is shown in FIGS. 3, 6, 8 and 9, reduces the size and bulk of the hinge while still maintaining the strength required by the jaws. However, the tissue engaging means can be placed in alternate arrangements with respect to the shaft member. For example, in FIG. 1, the tissue engaging means is arranged at approximately a 90° angle with respect to the shaft member.

In one embodiment of the invention, the shaft member is separable from the tissue engaging means. In use, the shaft member is utilized to place the tissue engaging means in the location desired. The shaft member is then released from the tissue engaging means and removed from the patient's body, leaving the tissue engaging means within the body. The tissue engaging means has a suture or tether attached to it, which extends out of the incision. When the tissue engaging means is to be removed, the shaft member is inserted back into the incision and is guided to the tissue engaging means by the suture or tether. The shaft member then is coupled to the tissue engaging means and the entire device is removed.

The jaws can be actuated by a number of different mechanisms, as shown in FIGS. 3, 6, 8, 9, and 10. Despite the use of a non-rigid shaft member, the present invention is capable of exerting a force on the tissue engaging means in the range of approximately 10–20 lbs. In the embodiment of FIG. 3, the hinged end of each jaw is provided with a reduced thickness portion 154, 155. In the open position of the tissue engaging means, shown in FIG. 3b, a jaw actuating member 156 mates with the reduced thickness portions of the jaws. In use, the handle assembly 112 is actuated, thereby pushing the actuating means 131 forward. The actuating means 131 in turn pushes the actuating member 156, thereby causing it to slide forward and out of the reduced thickness portions, as shown in FIG. 3a. This motion squeezes the jaws 146, 148 to the closed position while the reverse motion separates the jaws 146, 148 to the open position.

Figure 6A:
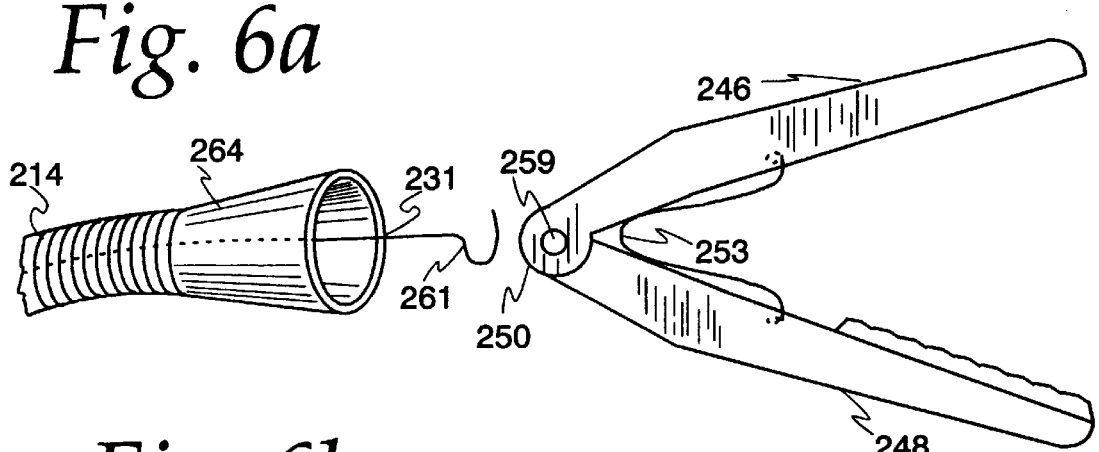
FIGS. 6a–6c are side views of an alternate embodiment of the jaw actuating mechanism made in accordance with the principles of the present invention.
Figure 6B:
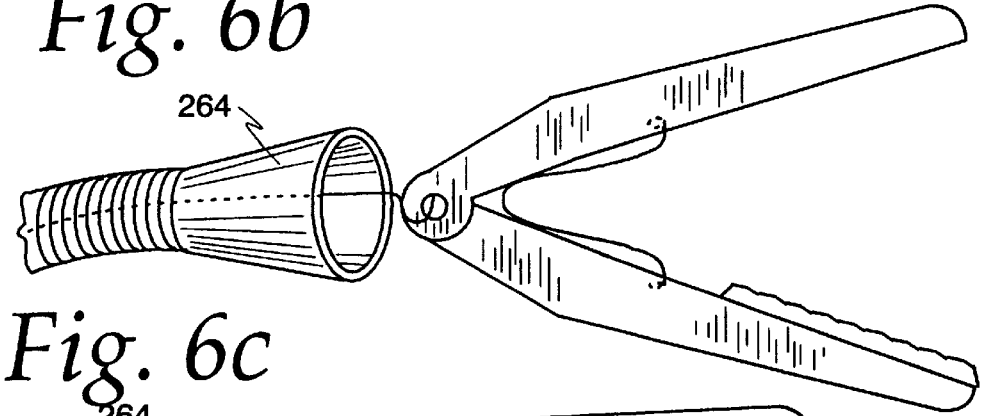
Figure 6C:
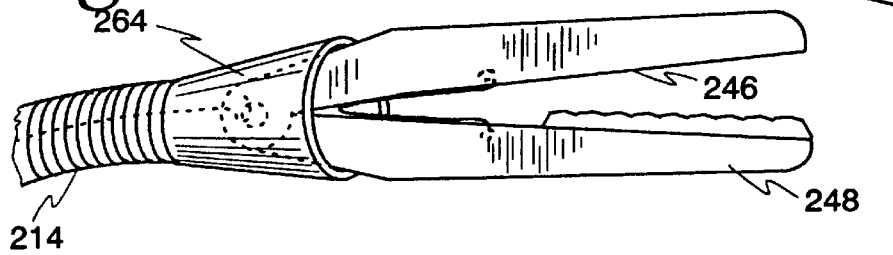

In the alternate embodiment of FIGS. 6a to 6c, the hinged end of each jaw is provided with a hole 259 which interacts with a hook 261 provided at the end of the actuating cable 231. Spring 253 is provided to maintain the jaws 246, 248 in the open position, as shown in FIG. 6a. To place the jaws 246, 248 in the closed position, the handle assembly is actuated, thereby pulling the cable 231 and hook 261 back through the shaft member 214. As the cable 231 is pulled back, the jaws 246, 248 are actuated to the closed position by their interaction with a conical end member 264 provided on the shaft member 214.

FIG. 8 depicts a further alternate embodiment of the jaw actuating mechanism. The mechanism includes a cylindrical clevis 520 having two longitudinal slots 522, 524 along its length, the slots located opposite of one another. The clevis 520 further includes a longitudinal cut-out 527 along its length. The jaws 546, 548 are disposed at one end of the clevis 520. The opposite end of the clevis 520 is provided with a cylindrical extension 529 through which the jaw actuating mechanism extends. In this embodiment, the jaw actuating mechanism comprises a wire driver 531 which extends through the cylindrical extension 529 and is operatively connected to one end of the jaws.

The jaws 546, 548 of this embodiment are provided with a diagonal slot 567, 569 at one end. As shown in FIG. 8b, the slotted ends of the jaws are disposed within the cut-out 527 of the clevis when the jaws are in the closed position. The jaws are attached along their median portion to the clevis by a screw 572 extending transversely across the longitudinal cut-out 527. The remainder of the jaws, the tissue engaging ends, extend from the clevis 521).

The end of the wire driver 531 which is coupled to the jaws 546, 548 is provided with a hook 561. As seen in FIG. 8a, a portion of the hook 561 is accommodated within each of the longitudinal slots. The remaining portion of the hook is coupled to the slots 567, 569 of the jaws. To actuate the jaws to an open position, the driver 531 is pushed toward the jaws. This motion causes the hook 561 to travel to one end of each of the slots 567, 569, thereby causing the jaws 546, 548 to pivot about the screw and move to the open position. As shown in FIG. 8, the slotted ends of the jaws extended outwardly from the longitudinal cut-out 527 when the jaws are in the open position. To return the jaws back to the closed position, the driver 531 is moved in the direction away from the jaws, thereby causing the driver to move to the opposite end of the slots 567, 569. The jaws again move about the screw to the closed position. In the closed position, the slotted ends of the jaws are within the cut-out 527. As can be seen by referring to FIGS. 8 and 8c, this type of actuating mechanism can be used with different tissue engaging means.

Figure 9:
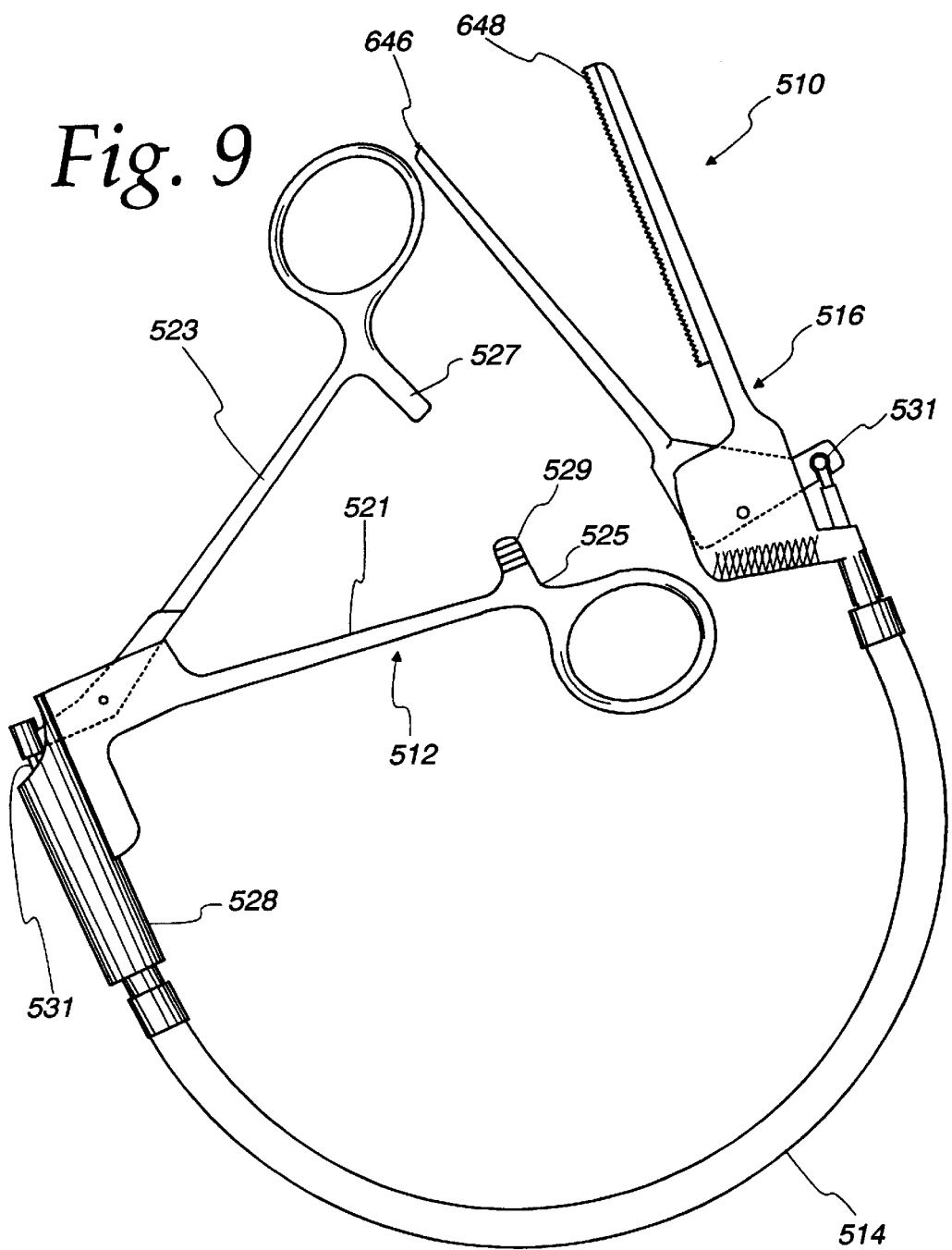
FIG. 9 is a perspective view of an alternate preferred embodiment made in accordance with the principles of the present invention.
Figure 9A:
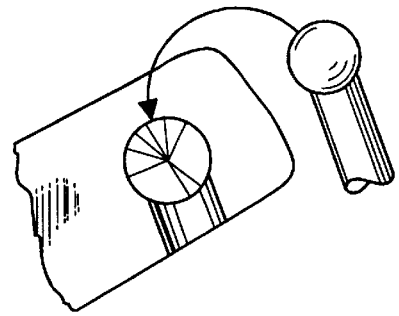
FIG. 9a is a detail view of the ball and socket arrangement used in the embodiment of FIG. 9.

A further preferred alternate embodiment of the present invention is depicted in FIG. 9. The surgical device 510 generally includes a handle assembly 512 comprising shaft support 528 and legs 521, 523, a shaft member 514 with an actuating cable 531 extending therethrough, and tissue engaging means 516 including jaws 646, 648. The actuating cable 531 is coupled to the leg 523 and to jaw 646 by a ball and socket arrangement, as mentioned above and as shown in detail in FIG. 9a. When leg 523 of the handle assembly is moved toward leg 521, this movement pulls on the actuating cable 53 1. The actuating cable 531 in turn pulls jaw 646, causing it to move toward jaw 648 and to the closed position. When it is desired to return the jaws to the opened position, leg 523 is released, thereby releasing the force on the cable and returning the jaws to the open position.

In the embodiment of FIG. 9, the shaft member 514 can take one of two forms. The shaft member 514 can comprise the dual-channeled tube, as discussed above arid shown in FIG. 5. Alternately, the shaft member can be comprised of tubing made of soft metal such as, for example, annealed stainless steel, brass or aluminum that is bendable and that can be placed in different shapes. In either instance, the shaft member is of a malleable type so that it can be placed in various arrangements to reach desired body locations.

In order to save the time and costs involved in sterilizing the surgical device and to reduce the cost and waste involved with fully disposable devices, the surgical device of the present invention can be made in part of disposable material so that the remainder of the surgical device is reusable. In one embodiment of the present invention, the tissue engaging means and the shaft member are made of disposable material, and a handle portion is made of re-useable material such as stainless steel. Alternately, only the tissue engaging means is made of disposable material, and the shaft member and the handle portion of re-useable material.

Figure 10:
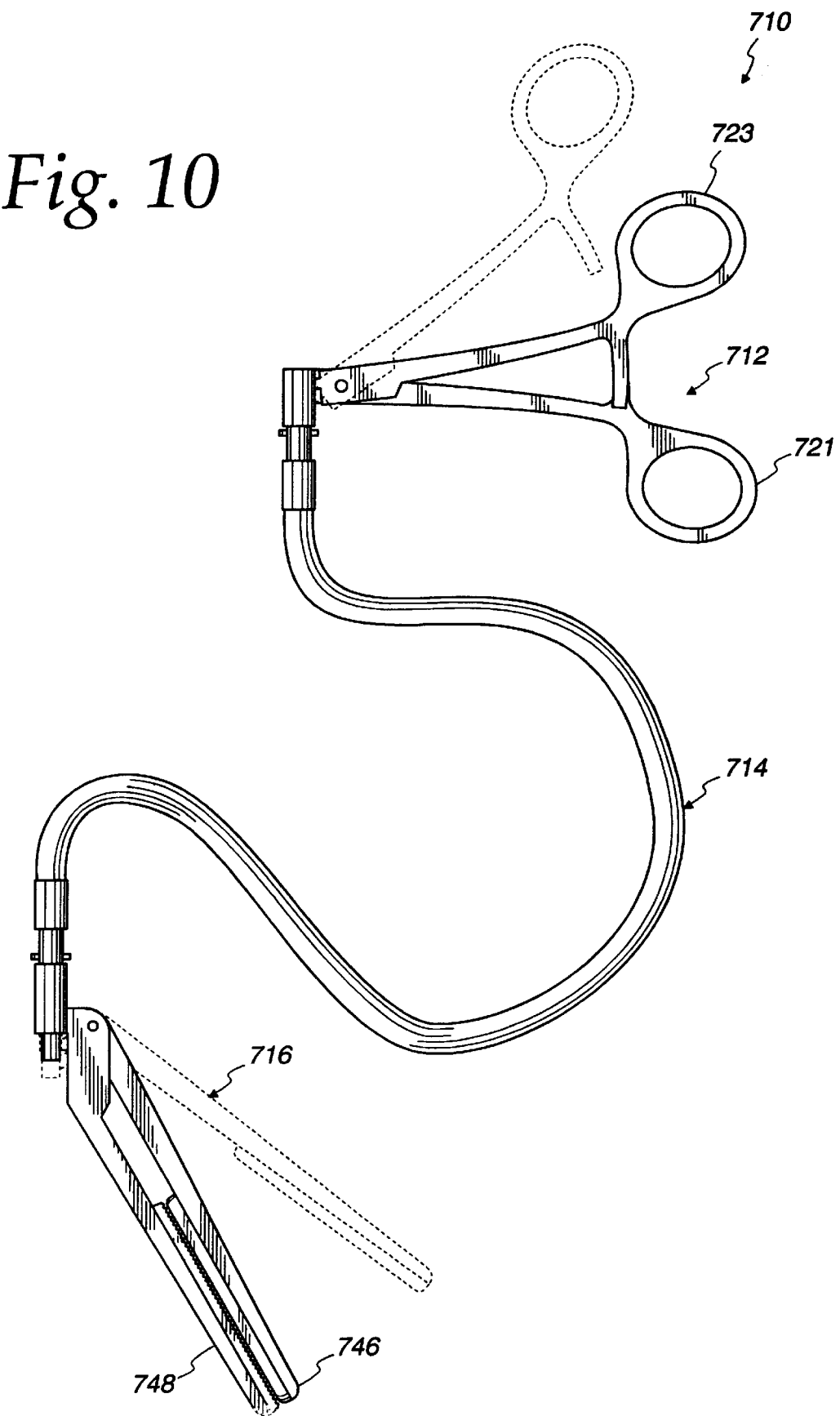
FIG. 10 is a perspective view of a disposable embodiment made in accordance with the principles of the present invention.

One such disposable device is shown in FIG. 10. The device 710 includes a disposable shaft member 714 operatively coupled to the tissue engaging means 716 and to the handle assembly 712, both made of re-useable material. The shaft member 714 is comprised of a malleable tube, preferably of a soft metal such as, for example, annealed stainless steel, brass or aluminum, having a plastic covering for cosmetic purposes. Alternately, the shaft member 714 is comprised of a malleable plastic tube, preferably of polyethylene or some other suitable plastic extrusion.

A jaw actuating means 731, comprising either a flexible cable or rod, extends through the tube 715, the actuating means 731 being capable of sliding freely within the tube. Each end of the actuating means 731 extends from a respective end of the malleable tube 715 and is provided with a spherical ball 720, 722 at its tip. As shown in FIGS. 11–14, both the tissue engaging means 716 and the handle assembly 712 are provided with a mating socket 724, 726 for the spherical ball 720, 722. As discussed below, the malleable tube 715 is coupled to the tissue engaging means 716 and to the handle assembly 712 by the mating of the spherical balls 720, 722 with the sockets 724, 726.

Figure 11:
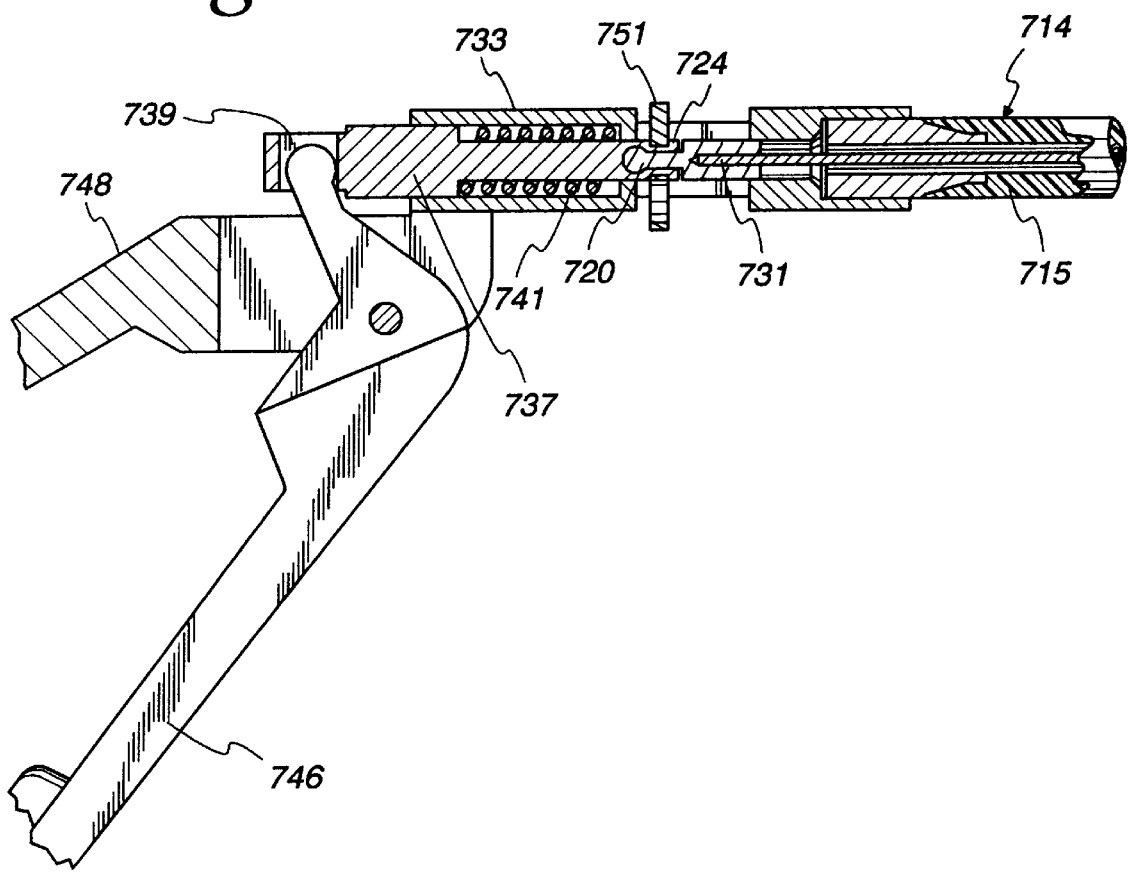
FIGS. 11 and 12 are cross-sectional views of the coupling arrangement between the jaw actuating means and the tissue engaging means of the embodiment of FIG. 10.
Figure 12:
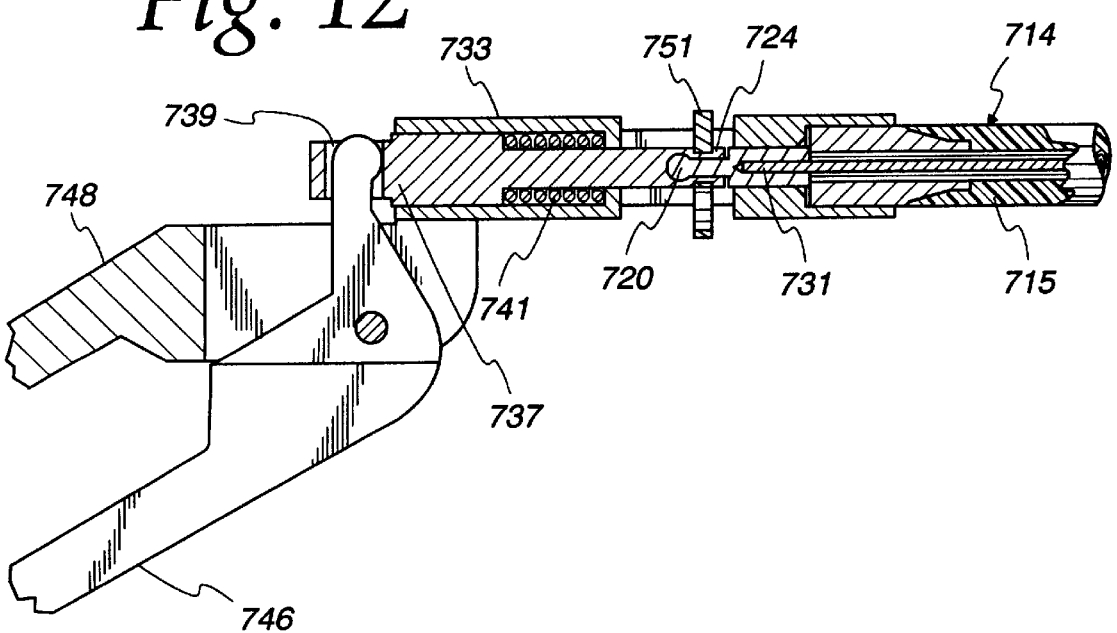

Referring to FIGS. 11 and 12, one of the jaws 748 of the tissue engaging means 716 is provided at one end with a cylinder 733. The other jaw 746 of the tissue engaging means 716 is provided with a bolt 737. The bolt 737 includes a cut-out portion 739 in which one end of jaw 746 pivots. The bolt 737 then extends away from jaw 746 through the cylinder 733 to mate with the jaw actuating means 731. As mentioned above, the bolt 737 is provided with the socket 724 which mates with the spherical ball 720 of the jaw actuating means 731. The (cylinder 733 is also provided with a spring 741 which biases the bolt 737 and in turn the jaw 746 to the open position. To actuate the jaws of the tissue engaging means from the open position shown in FIG. 11 to a closed position, the handle assembly 712 is actuated to pull one end of the jaw actuating means 731 in the direction away from the tissue engaging means 716,. Due to the ball and socket coupling, the bolt 737 is also pulled away from the tissue engaging means 716. This action causes the bolt 737 to act on jaw 746 via the cut-out portion 739, the jaw 746 pivoting to the closed position shown in FIG. 12. Since the jaws are spring biased to the open position, upon release of the pressure on the legs of the handle assembly, the jaws are returned to the open position.

Figure 13:
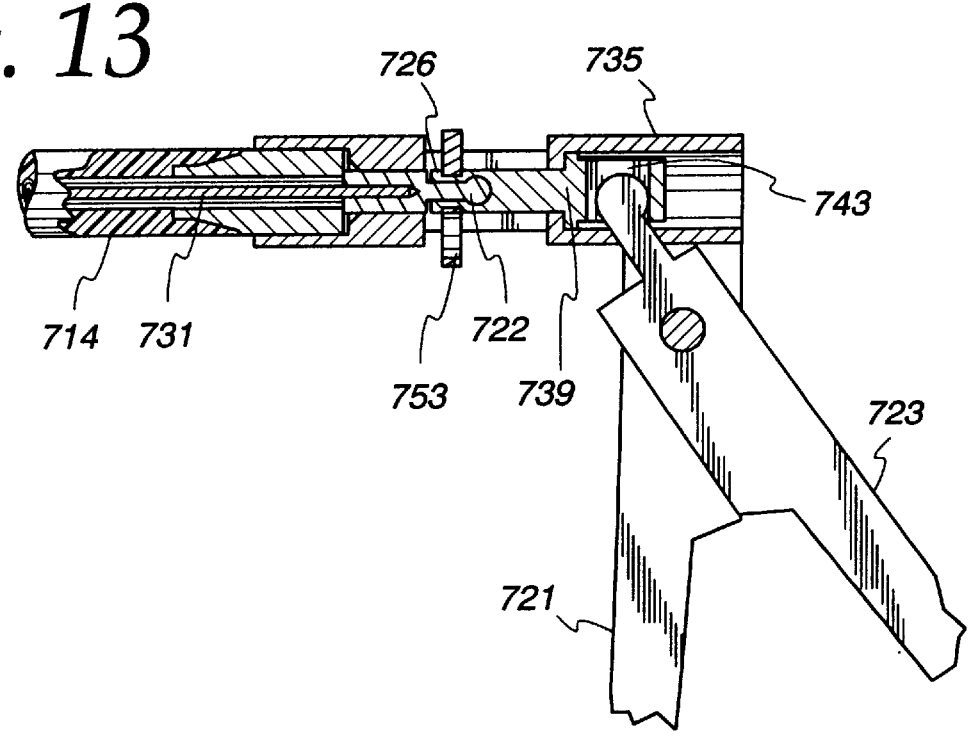
FIGS. 13 and 14 are cross-sectional views of the coupling arrangement between the jaw actuating means and the handle assembly of the embodiment of FIG. 10.
Figure 14:
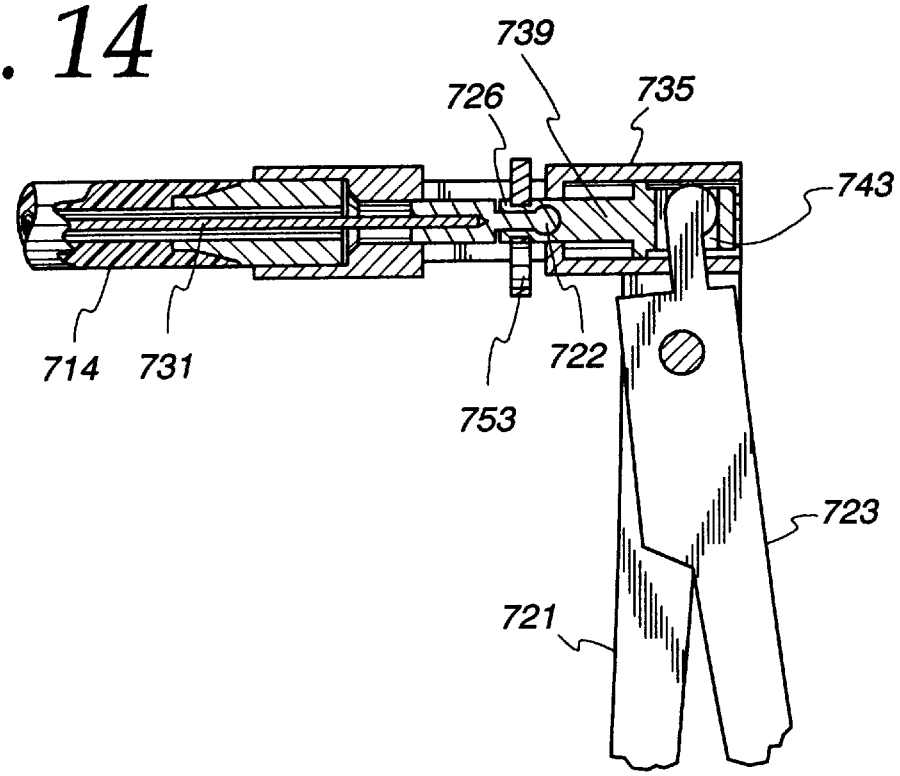

As shown in FIGS. 13 and 14, a similar ball and socket coupling is employed to couple the jaw actuating means 731 to the handle assembly 712. One of the legs of the handle assembly 712 is provided at one end with a cylinder 735 while the other leg 723 is provided with a bolt 739. The bolt 739 includes a cut-out portion 743 in which the end of leg 723 pivots. The bolt 739 then extends away from the leg 723 through the cylinder 735 to mate with the jaw actuating means 73 1. To mate with the spherical ball 722 of the jaw actuating means 731, the bolt 739 is provided with a socket 726. In order to actuate the tissue engaging means 716 to the closed position, the legs 721, 723 of the handle assembly 712 are moved from the position shown in FIG. 13, in which the legs are apart from one another, to the position shown in FIG. 14, in which the legs are brought together. With this action, leg 723 acts on the bolt 739 pulling it in a direction away from the tissue engaging means 716. The bolt 739 in turn acts on the jaw actuating means 731, pulling it in a direction away from the tissue engaging means 716. As discussed above, this action causes the opposite end of the jaw actuating means 731 to act on jaw 746 of the tissue engaging means 716, thereby bringing the jaws together to the, closed position, as shown in FIG. 12.

Figure 15A:
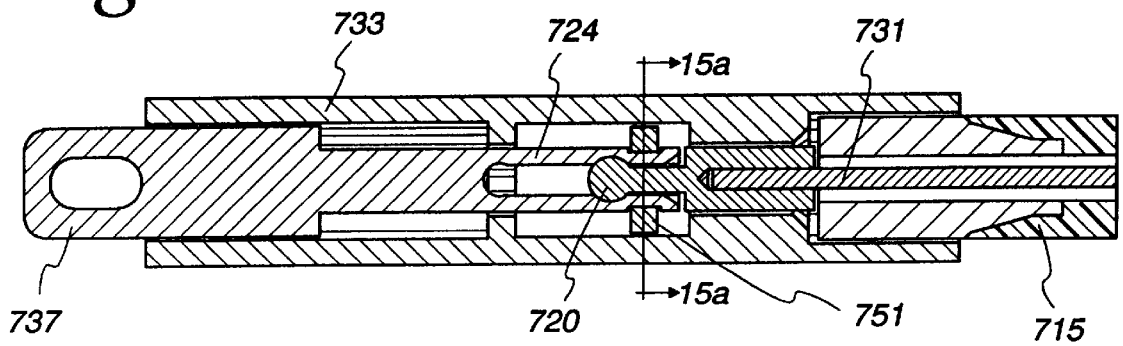
FIG. 15a is a cross-sectional view of the coupling arrangement of FIGS. 11 and 12, in —the locked position.
Figure 15B:
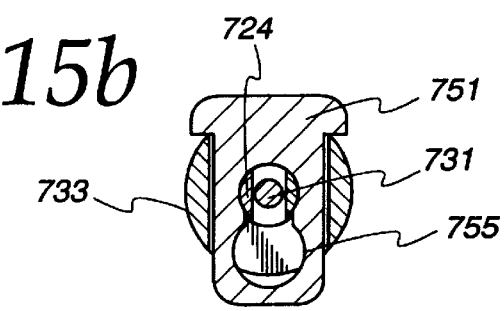
Figure 16A:
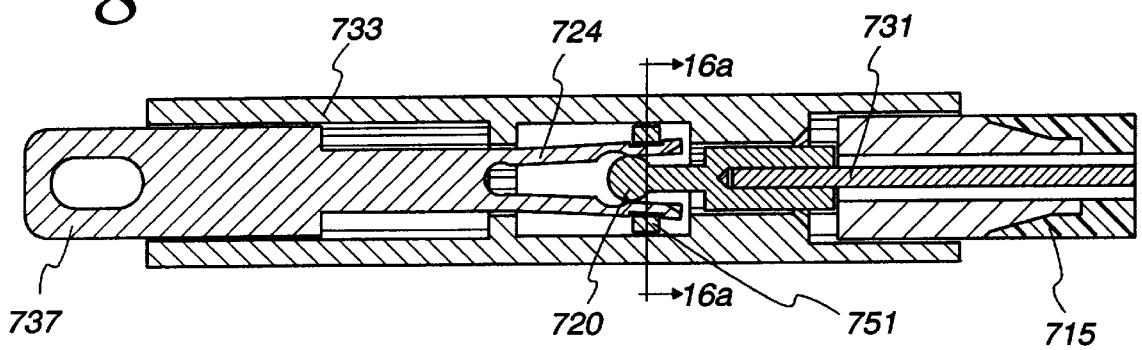
FIG. 16a is a cross-sectional view of the coupling arrangement of FIGS. 11 and 12, in the unlocked position.
Figure 16B:
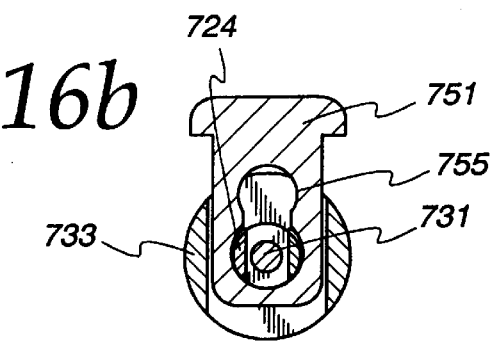

To enable the shaft member 714 to be separated from the handle assembly 712 and the tissue engaging means 716 and thus disposable, locking clips 751, 753 are provided at each ball and socket coupling. As seen from FIGS. 15b and 16b, each clip is provided with an opening 755 generally in the shape of the numeral "8." To lock the ball 720 of the jaw actuating means 731 to the socket 724 of the bolt 737, the locking clip 751 is placed in the position shown in FIG. 15b. To unlock the ball 720 of the jaw actuating means 731 from the socket 724 of the bolt 737 and thus allow the shaft member 714 to be separated and disposed, the locking clip 751 is placed in the position shown in FIG. 16b.

Figure 17:
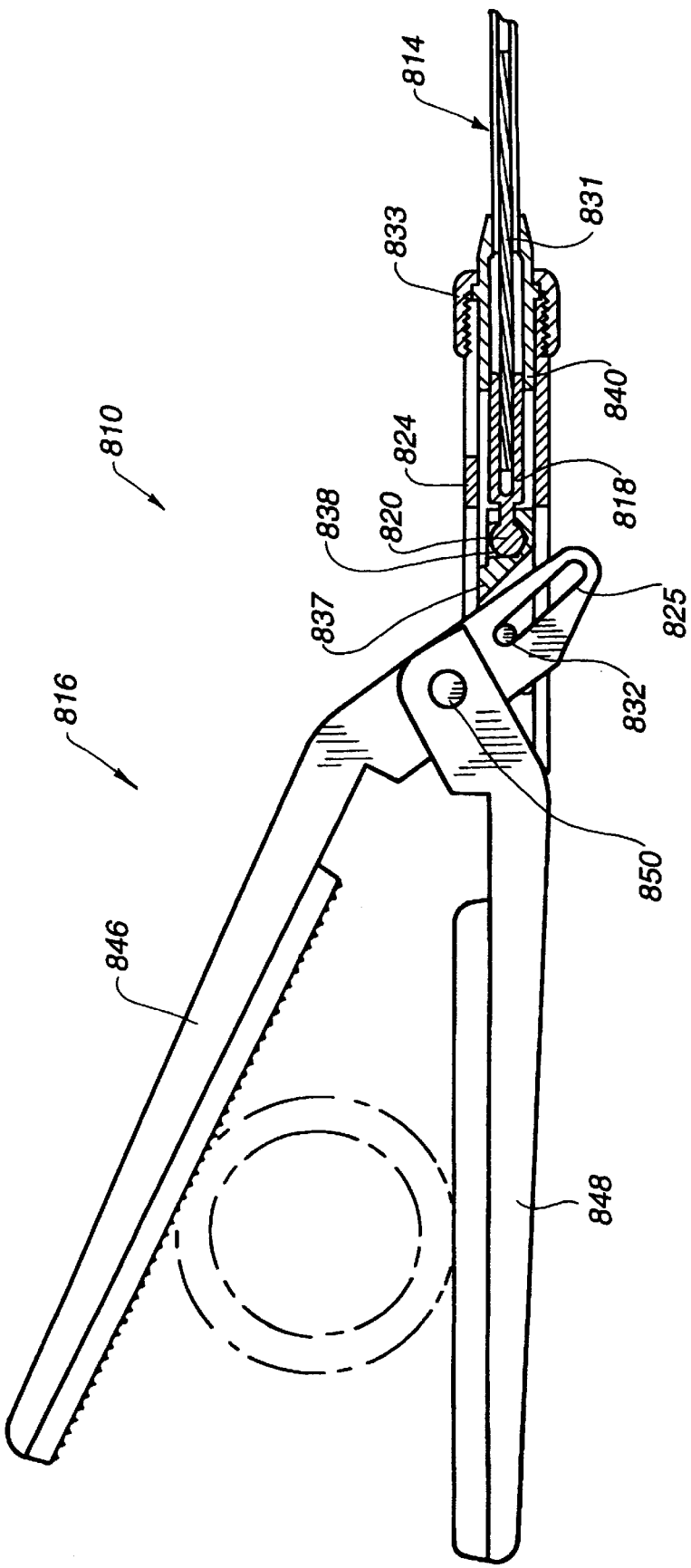
FIG. 17 is a cross-sectional view of an alternate embodiment of the jaw actuating mechanism made in accordance with the principles of the present invention.

Another preferred alternate embodiment of the present invention is depicted in FIGS. 17–19. The device 810 includes a tissue engaging means 816 with jaws 846, 848, a shaft member 814, and a handle assembly 812 with handles 821, 823. The shaft member 814 is comprised of a malleable tube, preferably of a soft metal such as, for example, annealed stainless steel, brass or aluminum. Each end of the shaft member is provided with a terminal member 840, 841. As shown in the figures, a jaw actuating means 831 comprising a cable extends through the shaft member 814. The jaw actuating means is provided at each end with a terminal member 818, 819, each terminal member having a spherical ball 820, 822 associated therewith.

Referring to FIGS. 17–17b, the tissue engaging means 816 is carried by a housing 824. Within the housing 824, a bolt member 837 moves, the bolt member being provided with a pin 832 and a socket 838 which cooperates with the spherical ball 820 of the jaw actuating means 831. Jaw 846 of the tissue engaging means is provided with a slot 825 which is operatively coupled to a bolt member 837 via pin 832. The shaft member 814 is coupled to the housing 824 by the cooperation between terminal member 840 and cap 833. To couple the shaft member with the housing, terminal member 840 is abutted against the housing 840 and the cap 833 is then attached to housing 824 via a suitable means such as screw threads.

To actuate the tissue engaging means from its open position, shown in FIG. 17, to its closed position, shown in FIG. 17b, the jaw actuating means is pulled in a direction away from the tissue engaging means. This movement in turn causes the bolt member 837 to move away from the tissue engaging means. As the bolt member moves away, the pin 832 travels from one end of the slot to the other, thereby causing the jaw to pivot about the fulcrum 950 to its closed position. The coupling arrangement between the jaw actuating means and the tissue engaging means allows the force required to remain relatively low, particularly when taking into consideration the long, thin configuration of the shaft member. Once the jaw actuating means is released, it moves back towards the jaw actuating means and the jaw 846 returns to its open position.

Referring to FIGS. 18–19, handle 821 of the handle assembly is provided at one end with a housing 852. Within the housing 852, a bolt member 839 moves, the bolt member 839 being provided with a socket 855 for coupling with the jaw actuating means and a cut-out portion 843 in which the end of leg 823 pivots. The shaft member 814 is coupled to the housing 852 by the cooperation between terminal member 841 and cap 834. To couple the shaft member 814 with the housing 852, terminal member 841 is abutted against the housing 852 and the cap 834 is then attached to housing 852 via a suitable means such as screw threads.

In order to actuate the tissue engaging means 816 to the closed position, the legs 821, 823 of the handle assembly 812 are moved from the position shown in FIG. 18, in which the legs are apart from one another, to the position shown in FIG. 19, in which the legs are brought together. With this action, leg 823 acts on the bolt member 839 pulling it in a direction away from the tissue engaging means 816. The bolt member 839 in turn acts on the jaw actuating means 831, pulling it in a direction away from the tissue engaging means 816. As discussed above, this action causes the opposite end of the jaw actuating means 831 to act on jaw 846 of the tissue engaging means 816, thereby bringing the jaws together to the closed position, as shown in FIG. 17b.

It should be understood that various changes in modifications to the preferred embodiment described herein will be apparent to those skilled in the art. Such changes and modifications can be made without departing from the spirit and scope of the present invention and without diminishing its attendant advantages. It is therefore intended that such changes and modifications be within the scope of the claims.

What is claimed is:

1. A surgical device having a longitudinal axis extending between a proximal end and a distal end, comprising:

tissue engaging means including first and second opposed jaws for grasping, securing, and occluding body tissue and conduits;

a shaft member operatively coupled to the tissue engaging means, the shaft member capable of being placed in different curvatures;

a handle assembly operatively coupled to the shaft member and to the, tissue engaging means; and a jaw actuating means for actuating the jaws of the tissue engaging means between an open position and a closed position, the actuating means being operatively connected to the tissue engaging means and to the handle assembly;

wherein the shaft member comprises a dual-channeled plastic tube having a first and a second channel, the jaw actuating means extending axially through the first channel and a malleable rod extending axially through the second channel.

2. The surgical device of claim 1 wherein the shaft member comprises a malleable tube with the jaw actuating means extending axially there through.

3. The surgical device of claim 1 wherein the shaft member comprises a series of interconnected ball and socket segments with the jaw actuating means extending axially there through.

4. The surgical device of claim 1 wherein the shaft member comprises soft metal tubing with the jaw actuating means extending axially there through.

5. The surgical device of claim 1 wherein the shaft member comprises wound metal tubing with the jaw actuating means extending axially there through.

6. The surgical device of claim 1 further comprising a compression return spring for biasing the tissue engaging means to an open position.

7. The surgical device of claim 1 wherein the tissue engaging means further includes a hinged end at which the jaws are hinged together.

8. The surgical device of claim 1 wherein the jaw actuating means comprises a drive rod.

9. The surgical device of claim 8 wherein a jaw actuating member is provided at the hinged end of the tissue engaging means for squeezing together the jaws of the tissue engaging means in response to actuation of the drive rod by the handle assembly.

10. The surgical device of claim 1 wherein the jaw actuating means comprises a cable.

11. The surgical device of claim 1 wherein the tissue engaging means and the shaft member are disposable.

12. The surgical device of claim 1 wherein the tissue engaging means is disposable.

13. The surgical device of claim 1 wherein the shaft member is disposable.

14. A surgical device having a longitudinal axis extending between a proximal end and a distal end, comprising:

tissue engaging means including first and second opposed jaws for grasping, securing and occluding body tissue and conduits, the tissue engaging means further including a hinged end at which the jaws are hinged together;

a shaft member operatively coupled to the tissue engaging means, the shaft member capable of being placed in different curvatures;

a handle assembly operatively coupled to the shaft member and to the tissue engaging means; and jaw actuating means for actuating the jaws of the tissue engaging means between an open position and a closed position, the jaw actuating means operatively connected to the tissue engaging means and to the handle assembly;

the hinged end of the tissue engaging means further including a hole there through, the hole interacting with a hook provided at one end of the jaw actuating means.

15. The surgical device of claim 14 wherein the shaft member is provided with a end member which, upon actuation of the cable by the handle assembly, interacts with the jaws of the tissue engaging means to bring the jaws to the closed position.

16. The surgical device of claim 14 wherein the shaft member comprises a malleable tube with the jaw actuating means extending axially there through.

17. The surgical device of claim 14 wherein the shaft member comprises a series of interconnected ball and socket segments with the jaw actuating means extending axially there through.

18. The surgical device of claim 14 wherein the shaft member comprises soft metal tubing with the jaw actuating means extending axially there through.

19. The surgical device of claim 14 wherein the shaft member comprises wound metal tubing with the jaw actuating means extending axially there through.

20. The surgical device of claim 14 further comprising a compression return spring for biasing the tissue engaging means to an open position.

21. The surgical device of claim 14 wherein the jaw actuating means comprises a drive rod.

22. The surgical device of claim 14 wherein a jaw actuating member is provided at the hinged end of the tissue engaging means for squeezing together the jaws of the tissue engaging means in response to actuation of the jaw actuating means by the handle assembly.

23. The surgical device of claim 14 wherein the jaw actuating means comprises a cable.

24. The surgical device of claim 14 wherein the shaft member is provided with an end member which, upon actuation of the cable by the handle assembly, interacts with the jaws of the tissue engaging means to bring the jaws to the closed position.

25. The surgical device of claim 14 wherein the jaw actuating means comprises a wire member having a hook at one end operatively coupled to the jaws of the tissue engaging means.

26. The surgical device of claim 25 wherein each jaw is provided with a diagonal slot at one end, the hook of the wire member interacting with the diagonal slots of the jaws to move the jaws between the open and closed positions.

27. The surgical device of claim 25 further provided with a clevis which houses a portion of the wire member and the slotted ends of the jaws.

28. The surgical device of claim 14 wherein one jaw of the tissue engaging means is provided with a slot at one end, the jaw actuating means being operatively coupled with the slot via a pin.

29. The surgical device of claim 14 wherein the tissue engaging means is further provided with a socket for coupling to the jaw, actuating means.

30. The surgical device of claim 29 wherein one end of the jaw actuating means is provided with a ball for coupling to the socket of the tissue engaging means.

31. The surgical device of claim 30 wherein another end of the jaw actuating means is provided with a ball for coupling to the handle assembly.

32. The surgical device of claim 14 wherein the tissue engaging means and the shaft member are disposable.

33. The surgical device of claim 14 wherein the tissue engaging means is disposable.

34. A surgical device having a longitudinal axis extending between a proximal end and a distal end, comprising:

tissue engaging means including first and second opposed jaws for grasping, securing, and occluding body tissue and conduits, the tissue engaging means further including, a hinged end at which the jaws are hinged together;

a shaft member operatively coupled to the tissue engaging means, the shaft member capable of being placed in different curvatures;

a handle assembly operatively coupled to the shaft member and to the tissue engaging means; and a jaw actuating means for actuating the jaws of the tissue engaging means between an open position and a closed position, the actuating means operatively connected to the tissue engaging means and to the handle assembly;

wherein the jaw actuating means comprises a wire member having a hook at one end operatively coupled to the jaws of the tissue engaging means.

35. The surgical device of claim 14 wherein the shaft member is disposable.

36. The surgical device of claim 34 wherein the shaft member comprises a malleable tube with the jaw actuating means extending axially there through.

37. The surgical device of claim 34 wherein the shaft member comprises a series of interconnected ball and socket segments with the jaw actuating means extending axially there through.

38. The surgical device of claim 34 wherein the shaft member comprises soft metal tubing with the jaw actuating means extending axially there through.

39. The surgical device of claim 34 wherein the shaft member comprises wound metal tubing with the jaw actuating means extending axially there through.

40. The surgical device of claim 34 wherein the shaft member comprises a dual channeled plastic tube having a first and a second channel, the jaw actuating means extending axially through the first channel and a malleable rod extending axially through the second channel.

41. The surgical device of claim 34 further comprising a compression return spring for biasing the tissue engaging means to an open position.

42. The surgical device of claim 34 wherein the jaw actuating means comprises a drive rod.

43. The surgical device of claim 34 wherein a jaw actuating member is provided at the hinged end of the tissue engaging means for squeezing together the jaws of the tissue engaging means in response to actuation of the jaw actuating means by the handle assembly.

44. The surgical device of claim 34 wherein the jaw actuating means comprises a cable.

45. The surgical device of claim 34 wherein the hinged end of the tissue engaging means includes a hole there through, the hole interacting with a hook provided at one end of the cable.

46. The surgical device of claim 34 wherein the shaft member is provided with an end member which, upon actuation of the cable by the handle assembly, interacts with the jaws of the tissue engaging means to bring the jaws to the closed position.

47. The surgical device of claim 34 wherein each jaw is provided with a diagonal slot at one end, the hook of the wire member interacting with the diagonal slots of the jaws to move the jaws between the open and closed positions.

48. The surgical device of claim 47 further provided with a clevis which houses a portion of the wire member and the slotted ends of the jaws.

49. The surgical device of claim 34 wherein one jaw of the tissue engaging means is provided with a slot at one end, the jaw actuating means being operatively coupled with the slot via a pin.

50. The surgical device of claim 34 wherein the tissue engaging means is further provided with a socket for coupling to the jaw actuating means.

51. The surgical device of claim 50 wherein one end of the, jaw actuating means is provided with a ball for coupling to the socket of the tissue engaging means.

52. The surgical device of claim 51 wherein another end of the jaw actuating means is provided with a ball for coupling to the handle assembly.

53. The surgical device of claim 34 wherein the tissue engaging means and the shaft member are disposable.

54. The surgical device of claim 34 wherein the tissue engaging means is disposable.

55. A surgical device having a longitudinal axis extending between a proximal end and a distal end, comprising:
  tissue engaging means including first and second opposed jaws for grasping, securing and occluding body tissue and conduits, the tissue engaging means further including a hinged end at which the jaws are hinged together;
  a shaft member operatively coupled to the tissue engaging means, the shaft member capable of being placed in different curvatures;
  a handle assembly operatively coupled to the shaft member and to the tissue engaging means; and
  a jaw actuating means for actuating the jaws of the tissue engaging means between an open position and a closed position, the actuating means operatively connected to the tissue engaging means and to the handle assembly;
  wherein at least one jaw is provided with a diagonal slot at one end, the jaw actuating means interacting with the diagonal slot of the jaw to move the jaws between the open and closed positions.

56. The surgical device of claim 55 further provided with a clevis which houses a portion of the wire member and the slotted ends of the jaws.

57. The surgical device of claim 34 wherein the shaft member is disposable.

58. The surgical device of claim 35 wherein the shaft member comprises a malleable tube with the jaw actuating means extending axially there through.

59. The surgical device of claim 35 wherein the shaft member comprises a series of interconnected ball and socket segments with the jaw actuating means extending axially there through.

60. The surgical device of claim 55 wherein the shaft member comprises soft metal tubing with the jaw actuating means extending axially there through.

61. The surgical device of claim 55 wherein the shaft member comprises wound metal tubing with the jaw actuating means extending axially there through.

62. The surgical device of claim 55 wherein the shaft member comprises a dual channeled plastic tube having a first and a second channel, the jaw actuating means extending axially through the first channel and a malleable rod extending axially through the second channel.

63. The surgical device of claim 55 further comprising a compression return spring for biasing the tissue engaging means to an open position.

64. The surgical device of claim 55 wherein the tissue engaging means further includes a hinged end at which the jaws are hinged together.

65. The surgical device of claim 55 wherein the jaw actuating means comprises a drive rod.

66. The surgical device of claim 55 wherein a jaw actuating member is provided at the hinged end of the tissue engaging means for squeezing together the jaws of the tissue engaging means in response to actuation of the jaw actuating means by the handle assembly.

67. The surgical device of claim 55 wherein the jaw actuating means comprises a cable.

68. The surgical device of claim 55 wherein the hinged end of the tissue engaging means includes a hole there through, the hole interacting with a hook provided at one end of the cable.

69. The surgical device of claim 55 wherein the shaft member is provided with an end member which, upon actuation of the cable by the handle assembly, interacts with the jaws of the tissue engaging means to bring the jaws to the closed position.

70. The surgical device of claim 55 wherein the jaw actuating means comprises a wire member having a hook at one end operatively coupled to the jaws of the tissue engaging means.

71. The surgical device of claim 55 further provided with a clevis which houses a portion of the jaw actuating means and the slotted ends of the jaws.

72. The surgical device of claim 55 wherein one jaw of the tissue engaging means is provided with a slot at one end, the jaw actuating means being operatively coupled.

73. The surgical device of claim 55 wherein the tissue engaging means is further provided with a socket for coupling to the jaw actuating means.

74. The surgical device of claim 73 wherein one end of the jaw actuating means is provided with a ball for coupling to the socket of the tissue engaging, means.

75. The surgical device of claim 74 wherein another end of the jaw actuating means is provided with a ball for coupling to the handle assembly.

76. The surgical device of claim 55 wherein the tissue engaging means and the shaft member are disposable.

77. The surgical device of claim 55 wherein the tissue engaging means is disposable.

78. A surgical device having a longitudinal axis extending between a proximal end and a distal end, comprising:

tissue engaging means including first and second opposed jaws for grasping, securing and occluding body tissue and conduits, the tissue engaging means further including a hinged end at which the jaws are hinged together;

a shaft member operatively coupled to the tissue engaging means, the shaft member capable of being placed in different curvatures;

a handle assembly operatively coupled to the shaft member and to the tissue engaging means; and jaw actuating means for actuating the jaws of the tissue engaging means between an open position and a closed position, the jaw actuating means operatively connected to the tissue engaging means and to the handle assembly;

wherein one jaw of the tissue engaging means is provided with a slot at one end, the jaw actuating means being operatively coupled with the slot via a pin.

79. The surgical device of claim 55 wherein the shaft member is disposable.

80. The surgical device of claim 78 wherein the shaft member comprises a malleable tube with the jaw actuating means extending axially there through.

81. The surgical device of claim 78 wherein the shaft member comprises a series of interconnected ball and socket segments with the jaw actuating means extending therethough.

82. The surgical device of claim 78 wherein the shaft member comprises soft metal tubing with the jaw actuating means extending axially there through.

83. The surgical device of claim 78 wherein the shaft member comprises wound metal tubing with the jaw actuating means extending axially there through.

84. The surgical device of claim 78 wherein the shaft member comprises a dualchanneled plastic tube having a first and a second channel, the jaw actuating means extending axially through the first channel and a malleable rod extending axially through the second channel.

85. The surgical device of claim 78 further comprising a compression return spring for biasing the tissue engaging means to an open position.

86. The surgical device of claim 78 wherein the tissue engaging means further includes a hinged end at which the jaws are hinged together.

87. The surgical device of claim 78 wherein the jaw actuating means comprises a drive rod.

88. The surgical device of claim 78 wherein a jaw actuating member is provided at the hinged end of the tissue engaging means for squeezing together the jaws of the tissue engaging means in response to actuation of the jaw actuating means by the handle assembly.

89. The surgical device of claim 78 wherein the jaw actuating means comprises a cable.

90. The surgical device of claim 78 wherein the hinged end of the tissue engaging means includes a hole there through, the hole interacting with a hook provided at one end of the cable.

91. The surgical device of claim 89 wherein the shaft member is provided with a end member which, upon actuation of the cable by the handle assembly, interacts with the jaws of the tissue engaging means to bring the jaws to the closed position.

92. The surgical device of claim 91 wherein the jaw actuating means comprises a wire member having a hook at one end operatively coupled to the jaws of the tissue engaging means.

93. The surgical device of claim 92 wherein each jaw is provided with a diagonal slot at one end, the hook of the wire member interacting with the diagonal slots of the jaws to move the jaws between the open and closed positions.

94. The surgical device of claim 93 further provided with a clevis which houses a portion of the wire member and the slotted ends of the jaws.

95. The surgical device of claim 78 wherein the tissue engaging means is further provided with a socket for coupling to the jaw actuating means.

96. The surgical device of claim 95 wherein one end of the jaw actuating means is provided with a ball for coupling to the socket of the tissue engaging means.

97. The surgical device of claim 96 wherein another end of the jaw actuating means is provided with a ball for coupling to the handle assembly.

98. The surgical device of claim 78 wherein the tissue engaging means and the shaft member are disposable.

99. The surgical device of claim 78 wherein the tissue engaging means is disposable.

100. A surgical device having a longitudinal axis extending between a proximal end and a distal end, comprising:

tissue engaging means including first and second opposed jaws for grasping, securing, and occluding body tissue and conduits, the tissue engaging means further including a hinged end at which the jaws are hinged together;

a shaft member operatively coupled to the tissue engaging means, them shaft member capable of being placed in different curvatures;

a handle assembly operatively coupled to the shaft member and to the tissue engaging means; and a jaw actuating means for actuating the jaws of the tissue engaging means between an open position and a closed position, the actuating means operatively connected to the tissue engaging means and to the handle assembly;

wherein the tissue engaging means is further provided with a socket for coupling to the jaw actuating means.

101. The surgical device of claim 100 wherein one end of the jaw actuating means is provided with a ball for coupling to the socket of the tissue engaging means.

102. The surgical device of claim 101 wherein another end of the jaw actuating means is provided with a ball for coupling to the handle assembly.

103. The surgical device of claim 78 wherein the shaft member is disposable.

104. The surgical device of claim 100 wherein the shaft member comprises a malleable tube with the jaw actuating means extending axially there through.

105. The surgical device of claim 100 wherein the shaft member comprises a series of interconnected ball and socket segments with the jaw actuating means extending axially there through.

106. The surgical device of claim 100 wherein the shaft member comprises soft metal tubing with the jaw actuating means extending axially there through.

107. The surgical device of claim 100 wherein the shaft member comprises wound metal tubing with the jaw actuating means extending axially there through.

108. The surgical device of claim 100 wherein the shaft member comprises a dual channeled plastic tube having a first and a second channel, the jaw actuating means extending axially through the first channel and a malleable rod extending axially through the second channel.

109. The surgical device of claim 100 further comprising a compression return spring for biasing the tissue engaging means to an open position.

110. The surgical device of claim 100 wherein the tissue engaging means further includes a hinged end at which the jaws are hinged together.

111. The surgical device of claim 100 wherein the jaw actuating means comprises a drive rod.

112. The surgical device of claim 100 wherein a jaw actuating member is provided at the hinged end of the tissue engaging means for squeezing together the jaws of the tissue engaging means in response to actuation of the jaw actuating means by the handle assembly.

113. The surgical device of claim 100 wherein the jaw actuating means comprises a cable.

114. The surgical device of claim 100 wherein the hinged end of the tissue engaging means includes a hole there through, the hole interacting with a hook provided at one end of the cable.

115. The surgical device of claim 100 wherein the shaft member is provided with a end member which, upon actuation of the cable by the handle assembly, interacts with the jaws of the tissue engaging means to bring the jaws to the closed position.

116. The surgical device of claim 100 wherein the jaw actuating means comprises a wire member having a hook at one end operatively coupled to the jaws of the tissue engaging means.

117. The surgical device of claim 116 wherein each jaw is provided with a diagonal slot at one end, the hook of the wire member interacting with the diagonal slots of the jaws to move the jaws between the open and closed positions.

118. The surgical device of claim 117 further provided with a clevis which houses a portion of the wire member and the slotted ends of the jaws.

119. The surgical device of claim 100 wherein one jaw of the tissue engaging means is provided with a slot at one end, the jaw actuating means being operatively coupled with the slot via a pin.

120. The surgical device of claim 119 wherein one end of the jaw actuating means is provided with a ball for coupling to the socket of the tissue, engaging means.

121. The surgical device of claim 120 wherein another end of the jaw actuating means is provided with a ball for coupling to the handle assembly.

122. The surgical device of claim 100 wherein the tissue engaging means and the shaft member are disposable.

123. The surgical device of claim 100 wherein the tissue engaging means is disposable.

124. A surgical device having a longitudinal axis extending between a proximal end and a distal end, comprising:
    tissue engaging means including first and second opposed jaws for grasping, securing, and occluding body tissue and conduits;
    a shaft member operatively coupled to the tissue engaging means, the shaft member capable of being placed and locked in different curvatures;
    a handle assembly operatively coupled to the shaft member and to the tissue engaging means;
    a jaw actuating means for actuating the jaws of the tissue engaging means between an open and a closed position; and
    a malleable applier instrument for grasping the jaws of the tissue engaging means for insertion together into an incision.

125. The surgical device claim 124 wherein the jaw actuating means comprising a cable operatively connected to the tissue engaging means, extending through the shaft member, and operatively connected to the handle assembly.

126. The surgical device claim 124 wherein the shaft member comprises a series of interconnected ball and socket segments with the jaw actuating cable extending axially there through.

127. The surgical device of claim 126 further comprising a tightening knob for exerting axial compression on the segments, thereby allowing the shaft member to be locked in any shape.

128. The surgical device claim 125 wherein the shaft member comprises a flexible tube with the jaw actuating cable extending axially there through.

129. The surgical device of claim 124 wherein the malleabke applier instrument is capable of being released and removed from the incision once the jaws of the tissue engaging means have been actuated to the closed position.

130. A surgical device having a longitudinal axis extending between a proximal end and a distal end, comprising:
    tissue engaging means including first and second opposed jaws for grasping, securing, and occluding body tissue and conduits, the tissue engaging means further provided with a socket;
    a shaft member operatively coupled to the tissue engaging means, the shaft member being constructed of malleable material and thus capable of being placed in different curvatures;
    a handle assembly operatively coupled to the shaft member and to the, tissue engaging means; and
    a jaw actuating means for actuating the jaws of the tissue engaging means between an open and a closed position, the jaw actuating means being couplable with them socket of the tissue engaging means, the tissue engaging means extending axially through the shaft member and being provided with coupling means at each end which enable the jaw actuating means and the shaft member to be separated from the remainder of the device to be disposed with a socket for coupling to the jaw actuating means.

131. The surgical device of claim 130 wherein the coupling means of the jaw actuating means comprises a first ball provided at one end of the actuating means for coupling with the socket of the tissue engaging means.

132. The surgical device of claim 131 wherein the coupling means of the jaw actuating means further comprises a second ball provided at another end of the jaw actuating means for coupling with the handle assembly.

133. The surgical device of claim 100 wherein the shaft member is disposable.

134. A surgical device having a longitudinal axis extending between a proximal end and a distal end, comprising:
    tissue engaging means including first and second opposed jaws for grasping, securing, and occluding body tissue and conduits, the tissue engaging means further including a hinged end at which the jaws are hinged together;
    a shaft member operatively coupled to the tissue engaging means, the shaft member including a series of interconnected ball and socket segments, the shaft member capable of being placed in different curvatures;
    a handle assembly operatively coupled to the shaft member and to the tissue engaging means; and
    a jaw actuating means for actuating the jaws of the tissue engaging means between an open position and a closed position, one end of the jaw actuating means being provided with a ball for coupling to a socket of the tissue engaging means and being operatively connected to the handle, assembly.

135. The surgical device of claim 134 further comprising a compression return spring for biasing the tissue engaging means to an open position.

136. The surgical device of claim 134 wherein the jaw actuating means comprises a drive rod.

137. The surgical device of claim 134 wherein a jaw actuating member is provided at the hinged end of the tissue engaging means for squeezing together the jaws of the tissue engaging means in response to actuation of the jaw actuating means by the handle assembly.

138. The surgical device of claim 134 wherein the jaw actuating means comprises a cable.

139. The surgical device of claim 134 wherein the hinged end of the tissue engaging means includes a hole there through, the hole interacting with a hook provided at one end of the cable.

140. The surgical device of claim 134 wherein the shaft member is provided with a end member which, upon actuation of the cable by the handle assembly, interacts with the jaws of the tissue engaging means to bring the jaws to the closed position.

141. The surgical device of claim 134 wherein the jaw actuating means comprises a wire member having a hook at one end operatively coupled to the jaws of the tissue engaging means.

142. The surgical device of claim 141 wherein each jaw is provided with a diagonal slot at one end, the hook of the wire member interacting with the diagonal slots of the jaws to move the jaws between the open and closed positions.

143. The surgical device of claim 141 further provided with a clevis which houses a portion of the wire member and the slotted ends of the jaws.

144. The surgical device of claim 134 wherein one jaw of the tissue engaging means is provide with a slot at one end, the jaw actuating means being operatively coupled with the slot via a pin.

145. The surgical device of claim 134 wherein the tissue engaging means and the shaft member are disposable.

146. The surgical device of claim 134 wherein the tissue engaging means is disposable.

147. The surgical device of claim 134 wherein the shaft member is disposable.

148. A surgical device having a longitudinal axis extending between a proximal end and a distal end, comprising:

tissue engaging means including first and second opposed jaws for grasping, securing, and occluding body tissue and conduits, the tissue engaging means further including a hinged end at which the jaws are hinged together, at least one jaw being provided with an actuating mechanism;

a malleable shaft member operatively coupled to the tissue engaging means, the shaft member capable of being placed in different curvatures;

a handle assembly operatively coupled to the shaft member and to the tissue engaging means; and a jaw actuating means for actuating the jaws of the tissue engaging means between an open position and a closed position, the actuating means operatively connected to the actuating mechanism on the jaw and to the handle assembly.

149. The surgical device of claim 148 wherein the shaft member comprises a malleable tube with the jaw actuating means extending axially there through.

150. The surgical device of claim 148 wherein the shaft member comprises soft metal tubing with the jaw actuating means extending axially there through.

151. The surgical device of claim 148 wherein the shaft member comprises wound metal tubing with the jaw actuating means extending axially there through.

152. The surgical device of claim 148 wherein the shaft member comprises a dual channeled plastic tube having a first and a second channel, the jaw actuating means extending axially through the first channel and a malleable rod extending axially through the second channel.

153. The surgical device of claim 148 further comprising ai compression return spring for biasing the tissue engaging means to an open position.

154. The surgical device of claim 148 wherein the jaw actuating means comprises a drive rod.

155. The surgical device of claim 148 wherein a jaw actuating member is provided at the hinged end of the tissue engaging means for squeezing together the jaws of the tissue engaging means in response to actuation of the jaw actuating means by the handle assembly.

156. The surgical device of claim 148 wherein the jaw actuating means comprises a cable.

157. The surgical device of claim 148 wherein the actuating member of the jaw includes a hole there through, the hole interacting with a hook provided at one end of the cable.

158. The surgical device of claim 148 wherein the shaft member is provided with a end member which, upon actuation of the cable by the handle assembly, interacts with the jaws of the tissue engaging means to bring the jaws to the closed position.

159. The surgical device of claim 148 wherein the jaw actuating means comprises a wire member having a hook at one end operatively coupled to the, actuating member of the jaw.

160. The surgical device of claim 159 wherein the actuating mechanism of the jaw is a diagonal slot, the hook of the wire member interacting with the diagonal slot of the jaw to move the jaws between the open and closed positions.

161. The surgical device of claim 160 further provided with a clevis which houses a portion of the wire member and the slotted end of the jaw.

162. The surgical device of claim 147 the actuating mechanism of the jaw is a slot, the jaw actuating means being operatively coupled with the slot via a pin.

163. The surgical device of claim 147 wherein the tissue engaging means and the shaft member are disposable.

164. The surgical device of claim 147 wherein the tissue engaging means is disposable.

165. The surgical device of claim 147 wherein the shaft member is disposable.

* * * * *

UNITED STATES PATENT AND TRADEMARK OFFICE
CERTIFICATE OF CORRECTION

PATENT NO. : 6,139,563
DATED : October 31, 2000
INVENTOR(S) : Cosgrove, III et al.

It is certified that error appears in the above-identified patent and that said Letters Patent is hereby corrected as shown below:

<u>Column 19, line 34 through Column 20, line 54,</u>
Please delete Claims 146-165.

Signed and Sealed this

Twenty-ninth Day of April, 2003

JAMES E. ROGAN
*Director of the United States Patent and Trademark Office*